United States Patent
Takahashi et al.

(10) Patent No.: US 11,918,184 B2
(45) Date of Patent: Mar. 5, 2024

(54) ENDOSCOPE ADAPTOR

(71) Applicant: MEDICAROID CORPORATION, Kobe (JP)

(72) Inventors: Kaoru Takahashi, Kobe (JP); Shota Betsugi, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 0 days.

(21) Appl. No.: 17/210,548

(22) Filed: Mar. 24, 2021

(65) Prior Publication Data
US 2021/0298574 A1 Sep. 30, 2021

(30) Foreign Application Priority Data

Mar. 30, 2020 (JP) .............................. JP2020-061175
Nov. 13, 2020 (JP) .............................. JP2020-189407

(51) Int. Cl.
*A61B 1/00* (2006.01)
*A61B 34/00* (2016.01)

(52) U.S. Cl.
CPC ...... *A61B 1/00121* (2013.01); *A61B 1/00002* (2013.01); *A61B 1/00117* (2013.01); *A61B 1/00147* (2013.01); *A61B 1/00149* (2013.01); *A61B 34/71* (2016.02)

(58) Field of Classification Search
CPC ............ A61B 1/00117; A61B 1/00121; A61B 1/00147
See application file for complete search history.

(56) References Cited

U.S. PATENT DOCUMENTS

| | | | | |
|---|---|---|---|---|
| 5,876,325 A | * | 3/1999 | Mizuno .................. | A61B 34/37 600/117 |
| 6,569,084 B1 | * | 5/2003 | Mizuno ................ | A61B 1/0051 600/102 |
| 10,238,457 B2 | | 3/2019 | Herrell et al. | |
| 2004/0049205 A1 | * | 3/2004 | Lee ......................... | A61B 34/37 606/130 |
| 2015/0105620 A1 | * | 4/2015 | Oginski ............. | A61B 1/00147 600/112 |
| 2019/0000560 A1 | | 1/2019 | Berman et al. | |
| 2020/0069382 A1 | | 3/2020 | Usuki et al. | |

FOREIGN PATENT DOCUMENTS

| | | |
|---|---|---|
| EP | 3616594 A1 | 3/2020 |
| JP | 2004-129956 A | 4/2004 |
| JP | 2020-031767 A | 3/2020 |
| WO | 2019/139941 A1 | 7/2019 |

* cited by examiner

*Primary Examiner* — Aaron B Fairchild
(74) *Attorney, Agent, or Firm* — METROLEX IP LAW GROUP, PLLC

(57) ABSTRACT

An endoscope adaptor according to an embodiment may include: an endoscope holder configured to hold an endoscope to be rotatable; and a base portion including an attachment portion, a driven member, and a transmission mechanism. The base portion includes a cable holder configured to hold a cable connected to the endoscope.

20 Claims, 17 Drawing Sheets

FIRST EMBODIMENT

CROSS SECTION ALONG LINE 301-301

FIRST STATE

SECOND STATE

SECOND EMBODIMENT

ENLARGED VIEW OF PORTION K

CROSS SECTION ALONG LINE 701-701

CROSS SECTION ALONG LINE 702-702

FIRST MODIFICATION

CROSS SECTION ALONG LINE 701-701

SECOND MODIFICATION

ENDOSCOPE ADAPTOR

CROSS REFERENCE TO RELATED APPLICATIONS

This application claims priority to Japanese Patent Application No 2020-061175 filed on Mar. 30, 2020 and Japanese Patent Application No 2020-189407 filed on Nov. 13, 2020, the entire contents of each of which are incorporated herein by reference.

BACKGROUND

The disclosure may relate to an endoscope adaptor and may especially relate to an endoscope adaptor that supports an endoscope.

In a related art, there is known an endoscope adaptor which supports an endoscope.

Japanese Patent Application Publication No 2004-129956 discloses an endoscope holding device that includes a mount portion including a permanent magnet that attracts and holds a holder portion of an endoscope, and a gear part that is housed in the mount portion and meshes with a gear provided in the holder portion of the endoscope. The endoscope holding device is configured, when the holder portion of the endoscope is attracted to the permanent magnet of the mount portion of the endoscope holding device, to mesh the gear part of the mount portion with the gear of the endoscope such that the endoscope can be rotated by driving the gear part.

SUMMARY

However, the endoscope holding device disclosed in Japanese Patent Application Publication No 2004-129956 is configured, when the holder portion of the endoscope is attracted to the permanent magnet of the mount portion of the endoscope holding device, to mesh the gear part of the mount portion with the gear of the endoscope such that the endoscope can be rotated by driving the gear part. With this configuration, if a drape for clean operation is provided between the mount portion and the endoscope, the gear part of the mount portion and the gear of the endoscope would not mesh with each other, and the endoscope cannot be rotated. Therefore, there may be a problem that it is difficult to rotatably hold the endoscope in a state where the endoscope holding device is covered with the drape.

An object of an embodiment of the disclosure may be to provide an endoscope adaptor capable of rotatably holding an endoscope in a state where a robot arm for holding the endoscope is covered with a drape.

An aspect of the disclosure may be an endoscope adaptor to be detachably connected to a robot arm of a robotic surgical system through a drape adaptor holding a drape. The endoscope adaptor may include: an endoscope holder configured to rotatably hold an endoscope; and a base portion that includes an attachment portion to be attached to the drape adaptor, a driven member configured to be driven to rotate by a drive part of the robot arm via the drape adaptor, and a transmission mechanism configured to transmit rotation of the driven member to the endoscope holder. The base portion further includes a cable holder configured to hold a cable connected to an endoscope.

According to the aspect of the disclosure, the rotation of the drive part of the robot arm can be transmitted to the endoscope holder that holds the endoscope through the drape adaptor in the state where the drape is provided between the robot arm and the drape adaptor, and thus the endoscope can be rotated. Therefore, the endoscope can be rotatably held in a state where the drape covers the robot arm that holds the endoscope. Further, according to the aspect, the endoscope adaptor is provided with the cable holder for holding the cable connected to the endoscope. Accordingly, with the cable holder holding the cable, it is possible to prevent the cable from being significantly swung when the endoscope is moved by the robot arm. As a result, when the endoscope is moved by the robot arm, the cable of the endoscope and the robot arm can be prevented from interfering with each other.

Note that another aspect of the disclosure may be an endoscope adaptor to be detachably connected to a robot arm of a robotic surgical system through a drape adaptor holding a drape. The endoscope adaptor may include: an endoscope holder configured to rotatably hold an endoscope; and a base portion that includes an attachment portion to be attached to the drape adaptor, a driven member configured to be driven to rotate by a drive part of the robot arm via the drape adaptor, and a transmission mechanism configured to transmit rotation of the driven member to the endoscope holder. A first gear is connected to the endoscope holder, and a second gear is connected to the driven member. The transmission mechanism includes: a third gear meshed with the first gear; a fourth gear meshed with the second gear; and a drive transmission shaft to which the third gear and the fourth gear are connected and which is configured to be rotated by rotation of the driven member. The base portion further includes a rotation prevention member configured to prevent the rotation of the endoscope holder when the driven member is not driven by the drive part of the robot arm.

DETAILED DESCRIPTION

Figure 1:
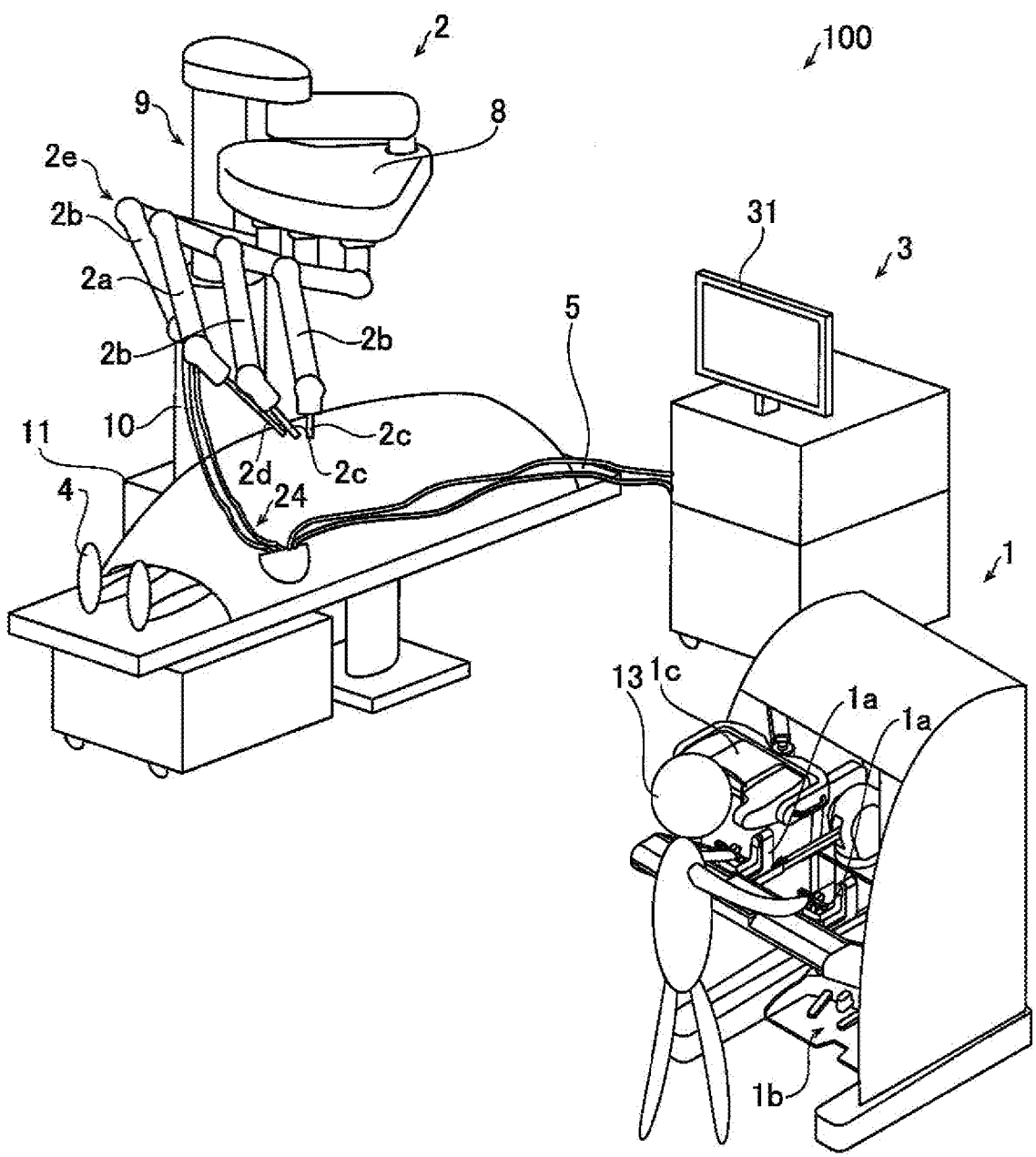
FIG. 1 is a diagram illustrating an overview of a robotic surgical system according to first and second embodiments.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

First Embodiment (Configuration of Robotic Surgical System)

A configuration of a robotic surgical system 100 according to a first embodiment is described with reference to FIGS. 1 and 2.

Figure 2:
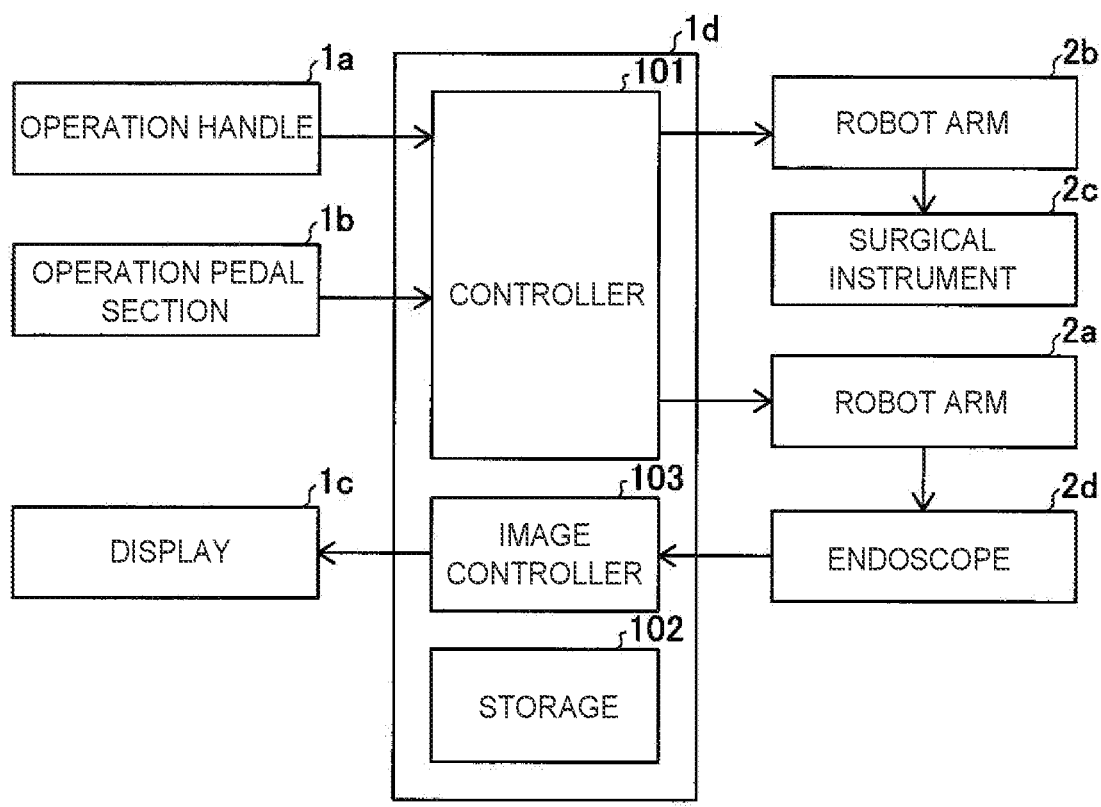
FIG. 2 is a block diagram illustrating a view of a control-related configuration of the robotic surgical system according to first and second embodiments.

As illustrated in FIGS. 1 and 2, the robotic surgical system 100 includes a remote control apparatus 1, a patient-side apparatus 2, and an image processing apparatus 3.

The remote control apparatus 1 is provided to remotely control medical equipment provided for the patient-side apparatus 2. When an operator 13, as a surgeon, inputs an action mode instruction to be executed by the patient-side apparatus 2, to the remote control apparatus 1, the remote control apparatus 1 transmits the action mode instruction to the patient-side apparatus 2 through a controller. In response to the action mode instruction transmitted from the remote control apparatus 1, the patient-side apparatus 2 operates medical equipment, including an endoscope 2d attached to a robot arm 2a and surgical instruments 2c attached to robot arms 2b. The image processing apparatus 3 transmits an image of a surgical field captured by the endoscope 2d to the remote control apparatus 1 or the like. This allows minimally invasive surgery.

The patient-side apparatus 2 constitutes an interface to perform a surgery for a patient 4. The patient-side apparatus 2 is positioned beside an operation table 5 on which the patient 4 is laid. The patient-side apparatus 2 includes plural robot arms 2e. One 2a of the robot arms 2e holds the endoscope 2d while the other robot arms 2b hold the surgical instruments 2c.

The patient-side apparatus 2 includes an endoscope adaptor 6 (see FIG. 3) for attaching the endoscope 2d to the robot arm 2a and an adaptor 7 (see FIG. 3) for attaching the endoscope adaptor 6 to the robot arm 2a. The robot arms 2e are commonly supported by a platform 8. Each of the plural robot arms 2e includes plural joints. Each joint includes a driver provided with a servo-motor and a position detector such as an encoder. The robot arms 2e are configured so that the medical equipment attached to each robot arm 2e is controlled by a driving signal given through the controller and performs a desired movement. Note that the adaptor 7 is an example of a drape adaptor. The adaptor 7 is also an adaptor for attaching the surgical instrument 2c to the robot arm 2b.

The platform 8 is supported by a positioner 9 placed on the floor of an operation room. The positioner 9 includes a column 10 and a base 11. The column 10 includes an elevating shaft adjustable in the vertical direction. The base 11 includes wheels and is movable on the floor surface.

To the distal end of the robot arm 2a, the endoscope 2d as the medical equipment is detachably attached. The endoscope 2d captures an image within the body cavity of the patient 4. The captured image is outputted to the remote control apparatus 1 through the image processing apparatus 3. The endoscope 2d may be a 3D endoscope capable of capturing a three-dimensional image or a 2D endoscope. In surgeries using the patient-side apparatus 2, the robot arm 2e introduces the endoscope 2d into the body of the patient 4 through a trocar placed on the body surface of the patient 4. The endoscope 2d is then located near the surgery site.

To the distal ends of the robot arm 2b, the surgical instrument 2c as the medical equipment is detachably attached. The surgical instrument 2c includes: a housing (not illustrated) which is attached to the robot arm 2b; an elongated shaft (not illustrated); and an end effector (not illustrated) which is provided on a side of the distal end of the shaft. The end effector is grasping forceps, scissors, a hook, a high-frequency knife, a snare wire, a clamp, a stapler, or the like, for example. The end effector is not limited to those and can be various types of treatment tools. In surgeries using the patient-side apparatus 2, the robot arms 2b introduce the surgical instruments 2c into the body of the patient 4 through a cannula (trocar) placed on the body surface of the patient 4. The end effectors of the surgical instruments 2c are then located near a surgery site.

The remote control apparatus 1 constitutes the interface with the operator 13. The remote control apparatus 1 is an apparatus that allows the operator 13 to operate medical equipment attached to the robot arms 2e. Specifically, the remote control apparatus 1 is configured to transmit action mode instructions which are inputted by the operator 13 and are to be executed by the surgical instruments 2c and endoscope 2d, to the patient-side apparatus 2 through the controller. The remote control apparatus 1 is installed beside the operation table 5 so that the operator 13 can see the condition of the patient 4 very well while operating the remote control apparatus 1 as a master apparatus, for example. The remote control apparatus 1 may be configured to transmit action mode instructions wirelessly and installed in a room different from the operation room where the operation table 5 is installed.

The action modes to be executed by the surgical instruments 2c include modes of actions to be taken by each surgical instrument 2c (a series of positions and postures) and actions to be executed by the function of each surgical instrument 2c. When the surgical instrument 2c is a pair of grasping forceps, for example, the action modes to be executed by the surgical instrument 2c include roll and pitch positions of the wrist of an end effector and actions to open and close the jaws. When the surgical instrument 2c is a high-frequency knife, the action modes to be executed by the surgical instrument 2c include vibration of the high-frequency knife, specifically, supply of current to the high-frequency knife. When the surgical instrument 2c is a snare wire, the action modes to be executed by the surgical instrument 2c include a capturing action and an action to release the captured object. Further the action modes may include an action to supply current to a bipolar or monopolar instrument to burn off the surgery site.

The action mode to be executed by the endoscope 2d includes setting of the position and posture of the tip of the endoscope 2d or setting of the zoom magnification of the endoscope 2d, for example.

As illustrated in FIGS. 1 and 2, the remote control apparatus 1 includes operation handles 1a, an operation pedal section 1b, a display 1c (or a display device), and a control apparatus 1d.

The operation handles 1a are provided in order to remotely operate medical equipment attached to the robot arms 2e. Specifically, the operation handles 1a accept operations by the operator 13 for operating the medical equipment (the surgical instruments 2c and the endoscope 2d). The operation handles 1a include two operation handles 1a arranged side by side in the horizontal direction. That is, one of the two operation handles 1a is operated by the right hand of the operator 13 while the other of the two operation handles 1a is operated by the left hand of the operator 13.

The operation handles 1a extend from the rear side of the remote control apparatus 1 toward the front side. The operation handles 1a are configured to move in a predetermined three-dimensional operation region. Specifically, the operation handles 1a are configured so as to move up and down, right and left, and forward and rearward.

The remote control apparatus 1 and the patient-side apparatus 2 constitute a master-slave system in terms of controlling movements of the robot arm 2a and the robot arms 2b. The operation handles 1a constitute an operating part on the master side in the master-slave system, and the robot arms 2a and 2b holding the medical equipment constitute an operating part on the slave side. When the operator 13 operates the operation handles 1a, the movement of the robot arm 2a or 2b is controlled so that the distal end portion (the endoscope 2d) of the robot arm 2a or the distal end portion (the end effector of the surgical instrument 2c) of the robot arm 2b moves following the movement of the operation handles 1a.

The patient-side apparatus 2 controls the movement of the robot arms 2b in accordance with the set motion scaling ratio. When the motion scaling ratio is set to ½, for example, the end effectors of the surgical instruments 2c move ½ of the movement distance of the operation handles 1a. This allows precise fine surgery.

The operation pedal section 1b includes plural pedals to execute medical equipment-related functions. The plural pedals include a coagulation pedal, a cutting pedal, a camera pedal, and a clutch pedal. The plural pedals are operated by a foot of the operator 13.

The coagulation pedal enables the surgical instrument 2c to coagulate the surgery site. Specifically, when the coagulation pedal is operated, voltage for coagulation is applied to the surgical instrument 2c to coagulate the surgery site. The cutting pedal enables the surgical instrument 2c to cut the surgery site. Specifically, the cutting pedal is operated to apply voltage for cutting to the surgical instrument 2c and cut the surgery site.

The camera pedal is used to control the position and orientation of the endoscope 2d that captures images within the body cavity. Specifically, the camera pedal enables control of the endoscope 2d by the operation handle 1a. That is, the position and orientation of the endoscope 2d are controllable by the operation handles 1a while the camera pedal is being pressed. The endoscope 2d is controlled by using both of the right and left operation handles 1a, for example. Specifically, when the operator 13 rotates the right and left operation handles 1a about the middle point between the right and left operation handles 1a, the endoscope 2d is rotated. When the operator 13 presses the right and left operation handles 1a together, the endoscope 2d goes further into the body cavity. When the operator 13 pulls the right and left operation handles 1a together, the endoscope 2d retracts. When the operator 13 moves the right and left operation handles 1a together up, down, right, and left, the endoscope 2d moves up, down, right, and left, respectively.

The clutch pedal is used to temporarily disconnect operation-related connection between the operation handles 1a and the robot arms 2e to stop movement of the surgical instruments 2c. Specifically, when the clutch pedal is being pressed, the robot arms 2e of the patient-side apparatus 2 do not work even if the operation handles 1a are operated. For example, when the operation handles 1a are operated and moved to the edge of the range of movement, the operator 13 operates the clutch pedal to temporarily disconnect the operation-related connection and then returns the operation handles 1a to the center of the range of movement. When the operator 13 stops operating the clutch pedal, the operation handles 1a are again connected to the robot arms 2e so that the operator 13 can restart the operation for the operation handles 1a around the center thereof.

The display 1c (or a display device) is configured to display images captured by the endoscope 2d. The display 1c is composed of a scope type display or a non-scope type display. The scope type display is a display configured in such a manner that the operator 13 looks into the display. The non-scope type display is a display like an open-type display that includes a flat screen and the operator 13 is able to see without looking into, such as normal displays for personal computers.

When the scope type display is attached, the scope type display displays 3D images captured by the endoscope 2d attached to the robot arm 2e of the patient-side apparatus 2. When the non-scope type display is attached, the non-scope type display also displays 3D images captured by the endoscope 2d provided for the patient-side apparatus 2. The non-scope type display may display 2D images captured by the endoscope 2d provided for the patient-side apparatus 2.

The control apparatus 1d includes a controller 101, a storage 102, and an image controller 103, for example. The controller 101 includes a calculator such as a CPU. The storage 102 includes a memory, such as a ROM and a RAM. The control apparatus 1d may be composed of a single controller performing centralized control or may be composed of plural controllers that perform decentralized control in cooperation with each other. The controller 101 determines whether an action mode instruction inputted by the operation handles 1a is to be executed by the robot arms 2b or to be executed by the endoscope 2d, depending on the state of the operation pedal section 1b. When determining that the action mode instruction inputted by the operation handles 1a is to be executed by any one of the surgical instruments 2c, the controller 101 transmits the action mode instruction to the corresponding robot arm 2b. The robot arm 2b is thereby driven for control of movement of the surgical instrument 2c attached to the robot arm 2b.

When determining that the action mode instruction inputted by the operation handles 1a is to be executed by the endoscope 2d, the controller 101 transmits the action mode instruction to the robot arm 2a. The robot arm 2a is thereby driven for controlling movement of the endoscope 2d attached to the robot arm 2a.

The storage 102 stores control programs corresponding to the types of the surgical instruments 2c, for example. The controller 101 reads the stored control programs according to the types of the attached surgical instruments 2c. The action mode instructions from the operation handles 1a and/or the operation pedal section 1b of the remote control apparatus 1 thereby cause the respective surgical instruments 2c to perform proper motions.

The image controller 103 transmits an image acquired by the endoscope 2d to the display 1c. The image controller 103 performs processing and correcting the images when needed.

The image processing apparatus 3 is configured to transmit the image obtained from the endoscope 2d to the remote control apparatus 1 and display the image obtained from the endoscope 2d. The image processing apparatus 3 performs processing and correcting the image obtained from the endoscope 2d when needed. Specifically, the image processing apparatus 3 includes an external monitor 31. The external monitor 31 is configured to be display the image captured by the endoscope 2d. The external monitor 31 is an open-type display section that includes a flat screen, such as normal displays for personal computers.

Figure 3:
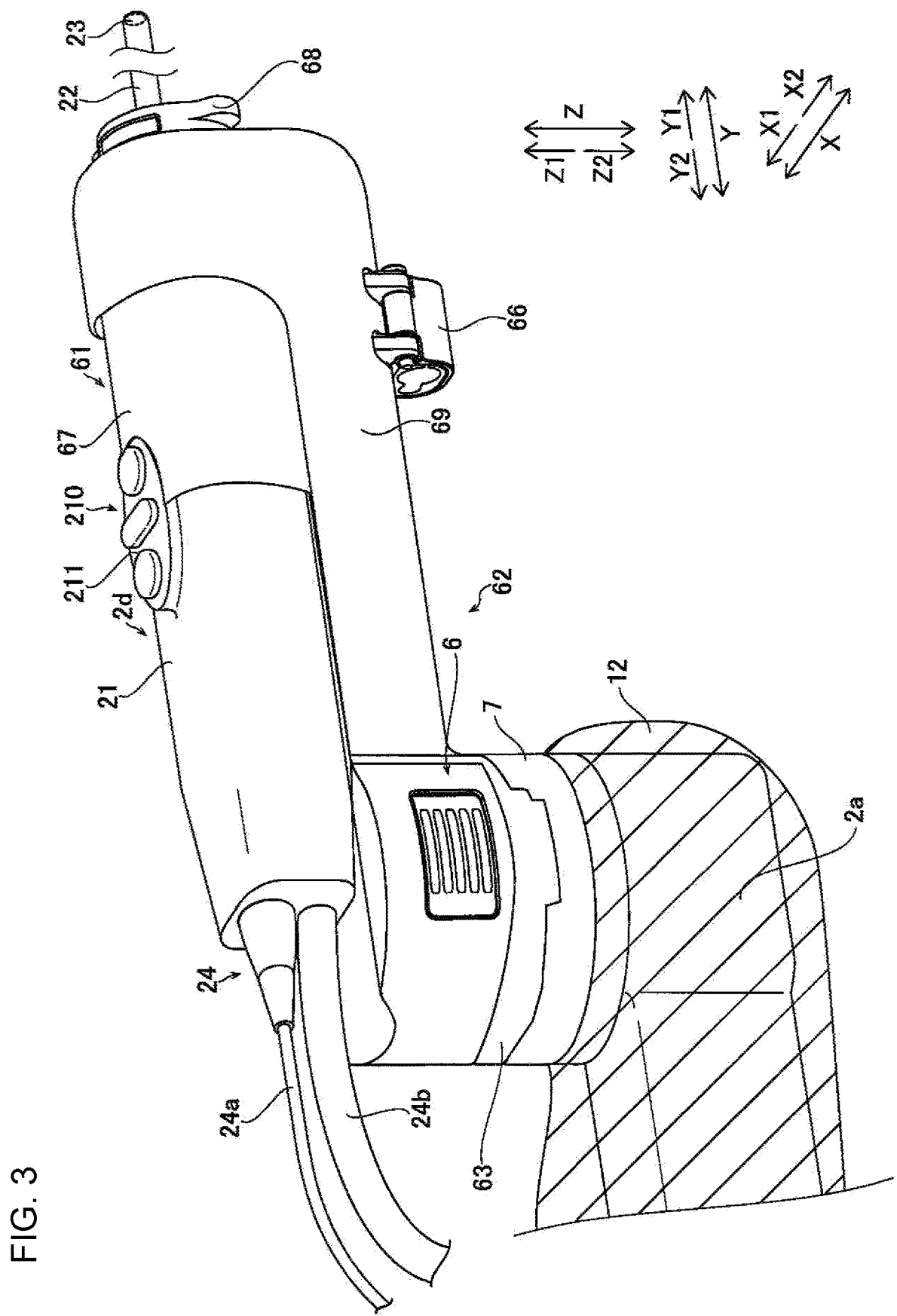
FIG. 3 is a diagram illustrating a perspective view of a state where an endoscope is attached to a robot arm through an endoscope adaptor according to first and second embodiments.

As illustrated in FIG. 3, the robot arms 2e are used in a clean area and thus are covered with drapes 12. In operation rooms, clean technique is used in order to prevent surgical incision sites and the medical equipment from being contaminated by pathogen, foreign matters, or the like. The clean technique defines a clean area and a contaminated area, which is outside the clean area. The surgery sites are located in the clean area. Members of the surgical team, including the operator 13, make sure that only sterile objects are placed in the clean area during surgery and perform sterilization for an object which is to be moved to the clean area from the contaminated area. Similarly, when the members of the surgical team including the operator 13 place their hands in the contaminated area, the members sterilize their hands before directly touching objects located in the clean area. Instruments used in the clean area are sterilized or are covered with the sterile drape 12.

Here, a direction in which the attachment portion 63 (described later) of the endoscope adaptor 6 and the endoscope 2d are arranged is referred to as a Z axis (Z direction). Along the Z axis, the endoscope 2d side and the attachment portion 63 side are respectively referred to as a Z1 direction (Z1 side) and a Z2 direction (Z2 side). Further, a direction in which a base portion 62 (described later) of the endoscope adaptor 6 extends is referred to as a Y axis (Y direction). Along the Y axis, a direction in which the endoscope 2d is inserted into the endoscope adaptor 6 is referred to as a Y1 direction (Y1 side) and the opposite direction of the Y1 direction is referred to as a Y2 direction (Y2 side). Further, a direction orthogonal to the Y direction and the Z direction is referred to as an X axis (X direction), one side along the X direction is referred as an X1 direction (X1 side), and the other side along the X direction is referred to as an X2 direction (X2 side).

The drape 12 is arranged between the adaptor 7 and the robot arm 2a(2b). The adaptor 7 is attached to the robot arm 2e in such a manner that the drape 12 is placed between the adaptor 7 and the robot arm 2e. Specifically, the adaptor 7 is a drape adaptor that puts the drape 12 between the adaptor 7 and the robot arm 2e.

The endoscope 2d is rotatably supported by the endoscope adaptor 6. The endoscope 2d is detachably attached to the endoscope adaptor 6. The endoscope 2d includes a main body 21, an elongate insertion part 22, and an imaging part 23. The endoscope 2d is supported by the endoscope adaptor 6 to be rotatable about a rotation axis C1 (see FIG. 5) along an extending direction (Y direction) of the insertion part 22. The rotation axis C1 is substantially aligned with the center line of the insertion part 22. The main body 21 has an elongate shape extending in the Z direction. The insertion part 22 is connected to one end of the main body 21, and cables 24 are connected to the other end of the main body 21.

The cables 24 includes a camera cable 24a for transmitting data of an image captured by the endoscope 2d and a light cable 24b for irradiating light when imaging the inside of a body cavity of a patient with the endoscope 2d. A diameter of the camera cable 24a is smaller than a diameter of the light cable 24b. The camera cable 24a is provided on the Z1 side with respect to the light cable 24b. As the endoscope 2d, a general-purpose endoscope may be used, or a dedicated endoscope for being attached to the robot arm 2a may be used.

The insertion part 22 is a part that is to be inserted in the body of the patient 4. The insertion part 22 has a hardness that is difficult to be deformed. That is, the endoscope 2d is a rigid endoscope. The insertion part 22 is to be inserted into the body of the patient 4 through a trocar placed on the body surface of the patient 4. To a distal end of the insertion part 22 (the end opposite to the side of the main body 21 of the endoscope), the imaging part 23 is provided. Accordingly, the imaging part 23 can be placed in the body of the patient 4 to capture an image of the surgical site in the body.

The imaging part 23 can capture an image by a single eye or plural eyes. That is, the imaging part 23 can image an object from a single position or multiple positions. The imaging part 23 is provided with illumination. The illumination is turned on to irradiate light to the imaging target upon imaging.

Figure 4:
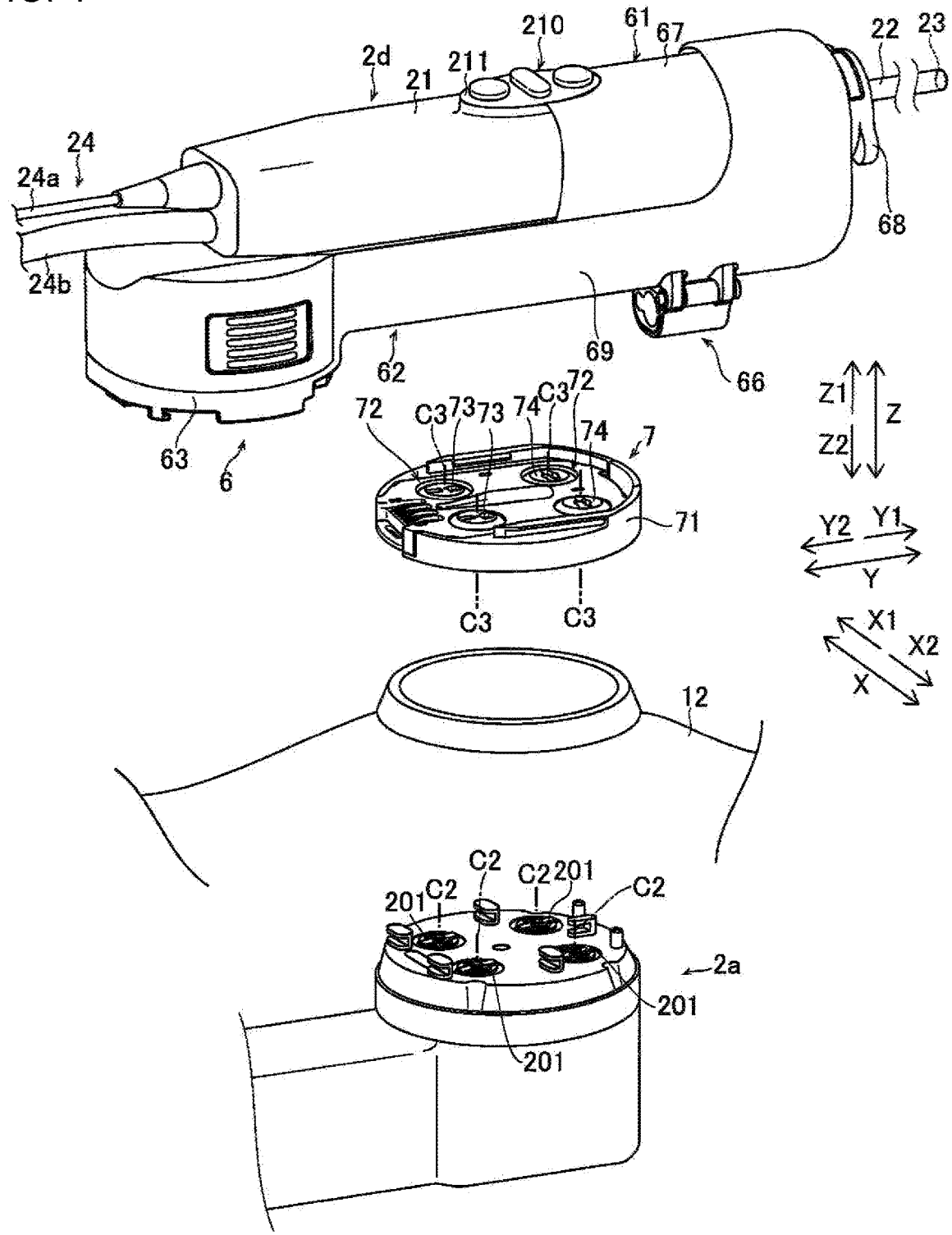
FIG. 4 is a diagram illustrating an exploded perspective view of a state where an adaptor and the endoscope adaptor are detached from the robot arm according to a first embodiment.
Figure 5:
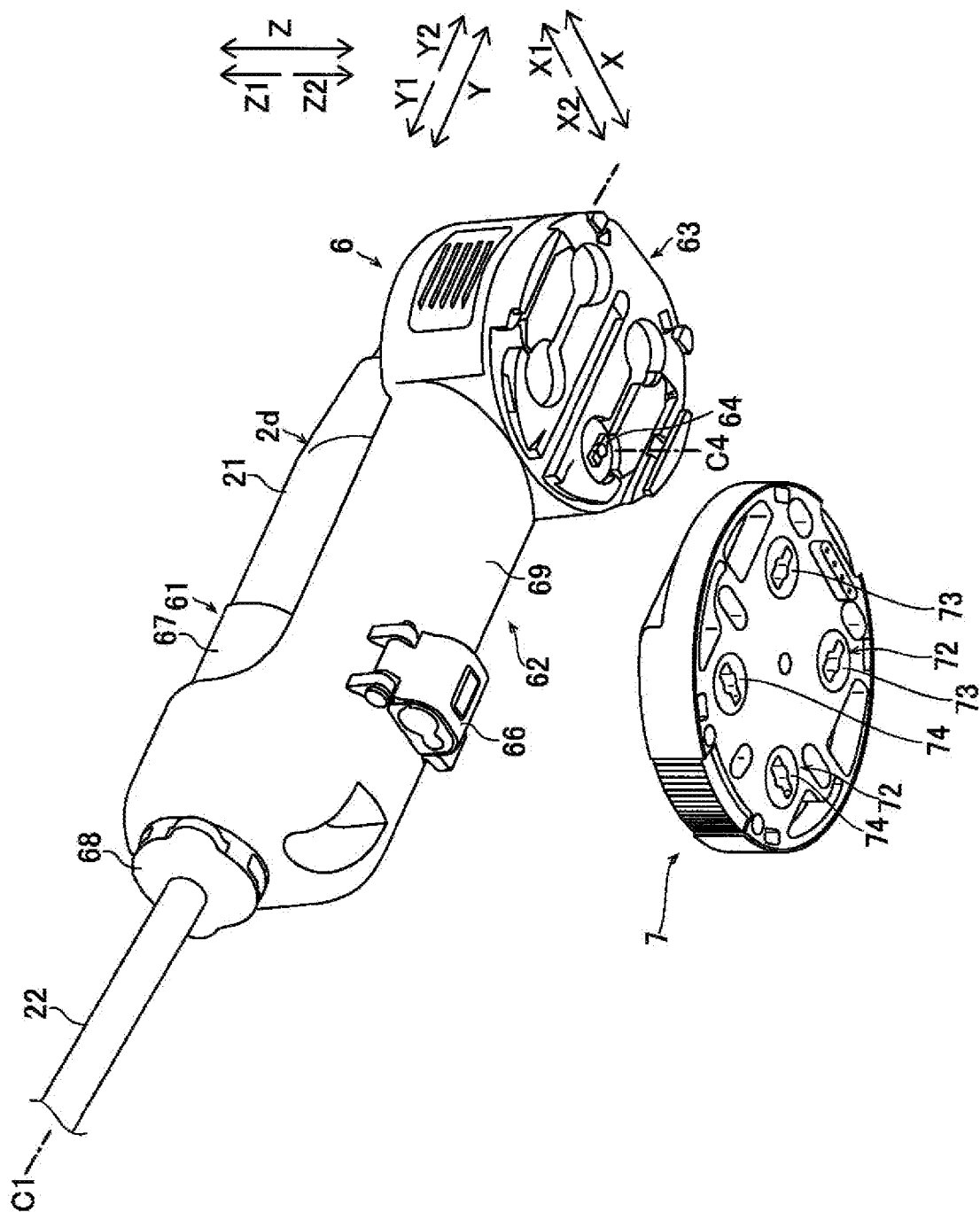
FIG. 5 is a diagram illustrating an exploded perspective view of the endoscope adaptor and the adaptor according to a first embodiment as seen from below.

As illustrated in FIGS. 4 and 5, in a state where the endoscope adaptor 6 is attached to the endoscope 2d, the endoscope 2d is connected to the robot arm 2a of the robotic surgical system 100 through the adaptor 7. The robot arm 2a transmits driving force to the endoscope adaptor 6 through the adaptor 7 to rotate the endoscope 2d. Specifically, the robot arm 2a is provided with rotational drive parts 201. The rotational drive part 201 is configured to be rotated about a rotation axis C2 extending in the Z direction by means of a drive source such as a motor or the like. Note that rotational drive part 201 is an example of a drive part.

The adaptor 7 includes a base body 71 and plural drive transmission members 72. The drive transmission members 72 include first drive transmission members 73 arranged in the Y2 side and second drive transmission members 74 arranged in the Y1 side. The drive transmission members 72 are rotatably provided in the base body 71. Specifically, the drive transmission members 72 are provided to be rotatable about rotation axes C3 extending in the Z direction. The drive transmission member 72 transmits driving force of the rotational drive part 201 of the robot arm 2a to a driven member 64 of the endoscope adaptor 6.

(Endoscope Adaptor)

The endoscope adaptor 6 according to a first embodiment is configured to bundle the cables 24 (see FIG. 1) by holding the cables 24 which hang down to the Y1 side. That is, to the endoscope 2d, the cable 24 for transmitting the image captured by the endoscope 2d is connected. The length of the cable 24 is set to be long enough with a margin. Thus, the endoscope adaptor 6 according to a first embodiment holds the cables, to prevent the cables 24 of the endoscope 2d from interfering with the robot arm 2a due to swing (movement) of the cables 24 when the endoscope 2d is moved by the robot arm 2a.

The endoscope adaptor 6 is detachably connected to the robot arm 2a of the robotic surgical system 100 via the adaptor 7 holding the drape 12. The endoscope adaptor 6 includes an endoscope holder 61 and a base portion 62. The endoscope holder 61 holds the endoscope 2d to be rotatable with respect to the base portion 62. In an embodiment, the endoscope holder 61 is attached to the base portion 62 to be rotatable with respect to the base portion 62. The base portion 62 includes an attachment portion 63 to be attached to the adaptor 7. The base portion 62 includes a driven member 64 which is provided on the attachment portion 63 and is rotationally driven by the rotational drive part 201 of the robot arm 2a via the adaptor 7. The base portion 62 includes a transmission mechanism 65 (see FIG. 14) configured to transmit rotation of the driven member 64 to the endoscope holder 61. The base portion 62 includes a cable holder 66 to hold the cables 24 connected to the endoscope 2d.

With this configuration, the rotation of the rotational drive part 201 of the robot arm 2a can be transmitted to the endoscope holder 61 that holds the endoscope 2d through the adaptor 7 in the state where the drape 12 is sandwiched between the robot arm 2a and the adaptor 7. Therefore, the endoscope 2d can be rotated about the rotation axis C1 extending in the direction in which the insertion part 22 extends. Therefore, the endoscope 2d can be rotatably held in a state where the drape 12 covers the robot arm 2a that holds the endoscope 2d. Further, the base portion 62 of the endoscope adaptor 6 is provided with a cable holder 66 for holding the cables 24 connected to the endoscope 2d. Accordingly, by holding the cables 24 with the cable holder 66, it is possible to prevent the cables 24 from being significantly swung when the endoscope 2d is moved by the robot arm 2a. As a result, when the endoscope 2d is moved by the robot arm 2a, the cables 24 of the endoscope 2d and the robot arm 2a can be prevented from interfering with each other.

In the following description of the endoscope adaptor 6, configurations of the endoscope holder 61, the base portion 62, the attachment portion 63, the driven member 64, the transmission mechanism 65, and the cable holder 66 are described in the recited order.

Figure 6:
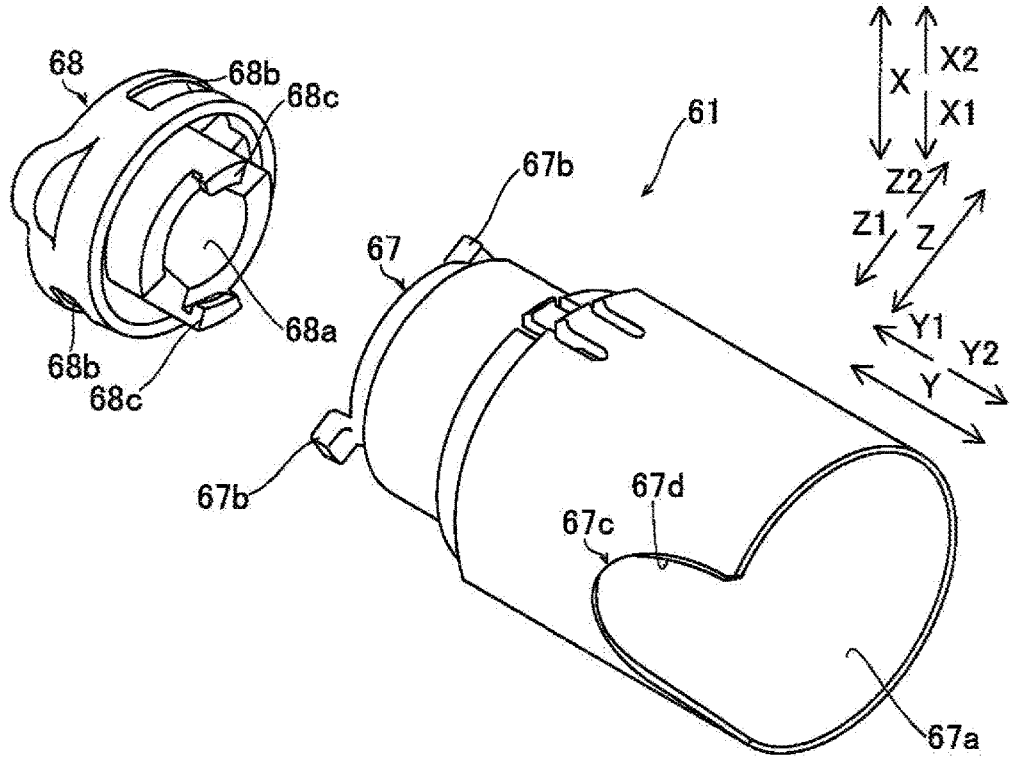
FIG. 6 is a diagram illustrating an exploded perspective view of an endoscope holder of the endoscope adaptor according to a first embodiment.
Figure 7:
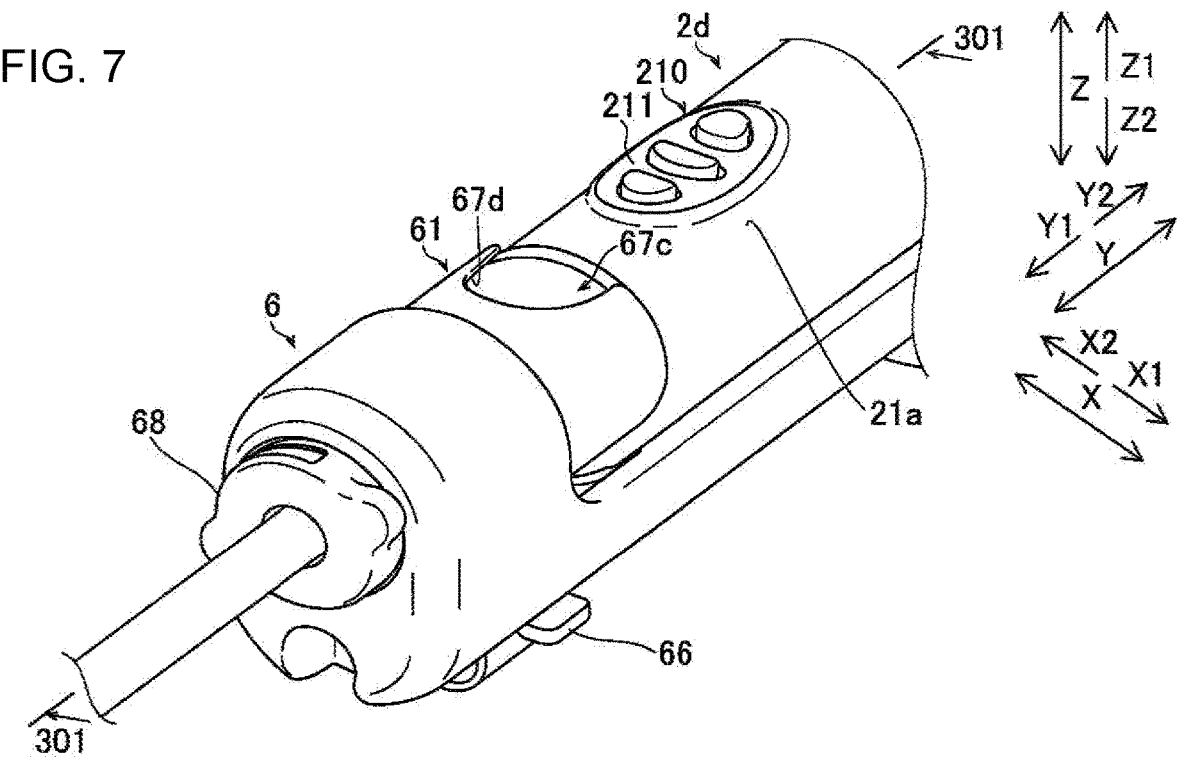
FIG. 7 is a diagram illustrating a perspective view of a part of the endoscope adaptor according to a first embodiment.

As illustrated in FIGS. 6 and 7, the endoscope holder 61 is configured to hold the endoscope 2d with being inserted in the endoscope holder 61. That is, the endoscope holder 61 is configured to attach the endoscope 2d to the base portion 62. Specifically, the endoscope holder 61 includes a holder main body 67 and a lock part 68.

The holder main body 67 has a substantially circular cylindrical shape. The holder main body 67 includes an insertion hole 67a to which the endoscope 2d is to be inserted. The insertion hole 67a penetrates through the holder main body 67 in the Y direction. The holder main body 67 includes a pair of engagement portions 67b to attach the lock part 68 to the holder main body 67. The pair of the engagement portions 67b are projected in a direction orthogonal to the Y direction. The holder main body 67 of the endoscope holder 61 is provided on the Y2 side with respect to the lock part 68 of the endoscope holder 61.

The endoscope holder 61 includes an engagement portion 67c to be engaged with an engagement portion 210 of the endoscope 2d.

With this, at the same time when the endoscope 2d is attached to the endoscope holder 61, the engagement portion 210 of the endoscope 2d and the engagement portion 67c of the endoscope holder 61 can be engaged with each other. Thus, the engagement portion 210 of the endoscope 2d and the engagement portion 67c of the endoscope holder 61 can be easily engaged.

Specifically, the engagement portion 67c is a notch 67d which is configured to be engaged with the convex (projected) operation part 211 serving as the engagement portion 210 projected from an outer circumferential surface 21a of the endoscope 2d and is recessed in the endoscope holder 61 toward the Y1 direction (the insertion direction of the endoscope) in which the endoscope 2d is inserted to the endoscope holder 61.

With this, the operation part 211 is projected from the outer surface 21a of the endoscope 2d, so that the operation part 211 is arranged at a position exposed to the outside and so that the notch 67d is also arranged at a position exposed to the outside. As a result, the operator can engage the operation part 211 with the notch 67d while visually recognizing the notch 67d and the operation part 211. Further, since the configuration for engaging the engagement portion 210 of the endoscope 2d and the engagement portion 67c of the endoscope holder 61 is provided by a simple structure using the operating part 211 of the endoscope 2d, it is possible to suppress the complexity of the structure of the endoscope holder 61.

Specifically, the notch 67d is recessed in a Y2 side end portion of the holder main body 67 toward the Y1 side. The notch 67d has a shape that matches a Y1 side portion of the operating portion 211 of the endoscope 2d when viewed from the Z1 side. That is, the notch 67d has a substantially U-shape when viewed from the Z1 side.

Figure 8:
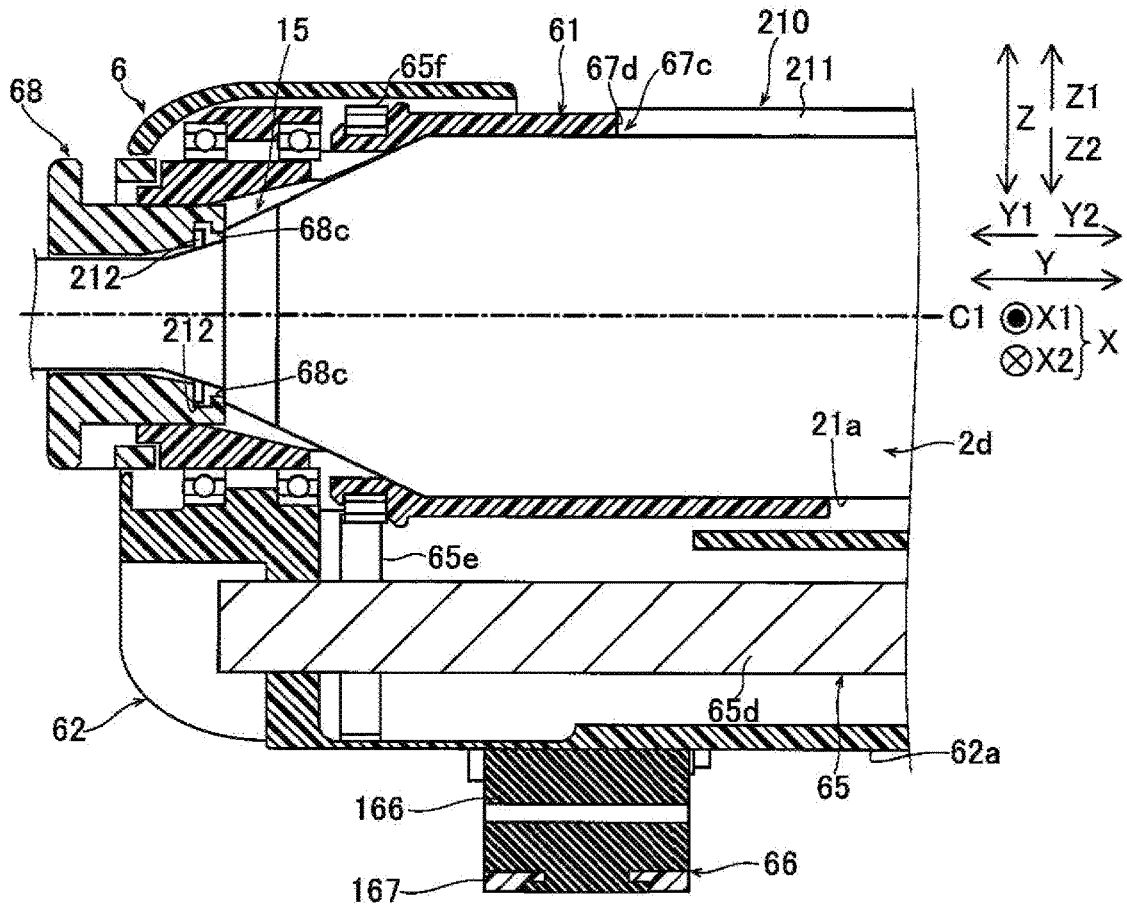
FIG. 8 is a diagram illustrating a part of a cross-sectional view taken along the 301-301 line in FIG. 7.

As illustrated in FIG. 8, the notch 67d is configured to position the endoscope 2d to a predetermined position 15 in the Y1 direction (the insertion direction) with the engagement portion 67c and the engagement portion 210 being engaged with each other.

Accordingly, not only the engagement portion 67c and the engagement portion 210 of the endoscope 2d can be engaged, but also the positioning of the endoscope 2d can be performed. Therefore, compared to a case where a structure for engaging the engagement portion 67c and the engagement portion 210 and a structure for positioning the endoscope 2d are provided separately, it is possible to suppress the increase in size of the endoscope holder 61.

Here, the predetermined position 15 is a position where the endoscope 2d is inserted into the endoscope holder 61 and the endoscope 2d is positioned in the Y direction by the lock part 68. The notch 67d is also configured to position the endoscope 2d in the circumferential direction about the rotational axis C1 extending along the Y direction in the state where the engagement portion 67c and the engagement portion 210 are engaged with each other.

As illustrated in FIG. 6, the lock part 68 includes an insertion hole 68a to which a distal end portion of the main body 21 of the endoscope 2d is inserted. The insertion hole 68a penetrates through the lock part 68 in the Y direction. The lock part 68 includes a pair of engagement holes 68b to be engaged with a pair of engagement portions 67b of the holder main body 67. The pair of the engagement holes 68b penetrate the lock part 68 in a direction orthogonal to the Y direction. The lock part 68 is provided on the Y1 side with respect to the holder main body 67.

As illustrated in FIGS. 7 and 8, the endoscope 2d includes an endoscope-side protrusion 212 that protrudes in a direction orthogonal to the direction of the rotation axis C1 of the endoscope 2d, whereas the endoscope holder 61 includes a holder-side protrusion 68c that protrudes in the direction opposite to the protruding direction of the endoscope-side protrusion 212 and is to be engaged with the endoscope-side protrusion 212 of the endoscope 2d. The holder-side protrusion 68c is configured to generate a sound upon engaging with and disengaging from the endoscope-side protrusion 212.

Accordingly, the operator can confirm the engagement and the disengagement of the endoscope 2d to and from the endoscope holder 61 by sound, so that the operator can surely perform the engagement and the disengagement between the endoscope 2d and the endoscope holder 61.

Specifically, the holder-side protrusion 68c projects inwardly from the endoscope holder 61 in the radial direction of the endoscope 2d. The holder-side protrusion 68c is provided at a Y2 side end portion of the lock part 68 of the endoscope holder 61. The holder-side protrusion 68c and the endoscope-side protrusion 212 overlap with each other when viewed from the Y2 side. The holder-side protrusion 68c and the endoscope-side protrusion 212 are engaged with each other in the Y direction. A plurality (two) of the holder-side protrusions 68c are provided.

As illustrated in FIGS. 9 to 12, the holder-side protrusion 68c is configured to be elastically deformed by abutting on the endoscope-side protrusion 212 and to generate a sound when the holder-side protrusion 68c moves over the endoscope-side protrusion 212 to engage with or disengage from the endoscope-side protrusion 212.

Accordingly, the sound can be generated when the endoscope 2d and the endoscope holder 61 are engaged or disengaged by utilizing the elastic deformation of the holder-side protrusion 68c. A structure for generating a sound when the endoscope 2d and the endoscope holder 61 are engaged or disengaged can be realized by a simple structure. As a result, it is possible to suppress the complexity of the structure of the endoscope holder 61 for generating a sound when the endoscope 2d and the endoscope holder 61 are engaged or disengaged.

Figure 9:
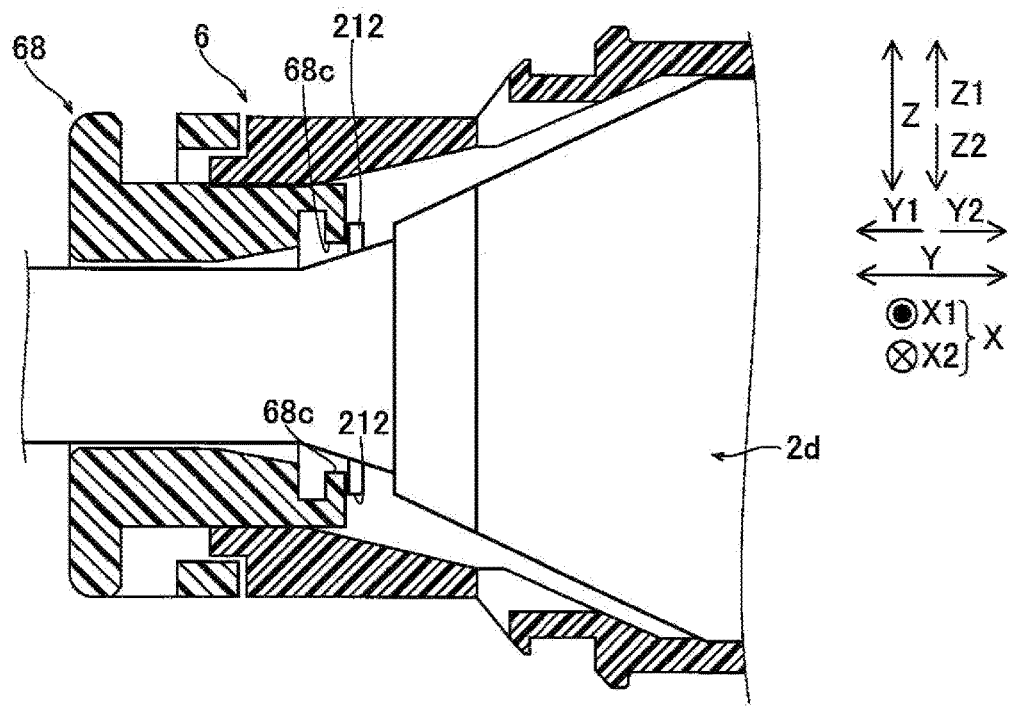
FIG. 9 is a diagram illustrating a cross sectional view of the K part in FIG. 8 illustrating a state where the endoscope is inserted in the endoscope holder of the endoscope adaptor according to a first embodiment.
Figure 10:
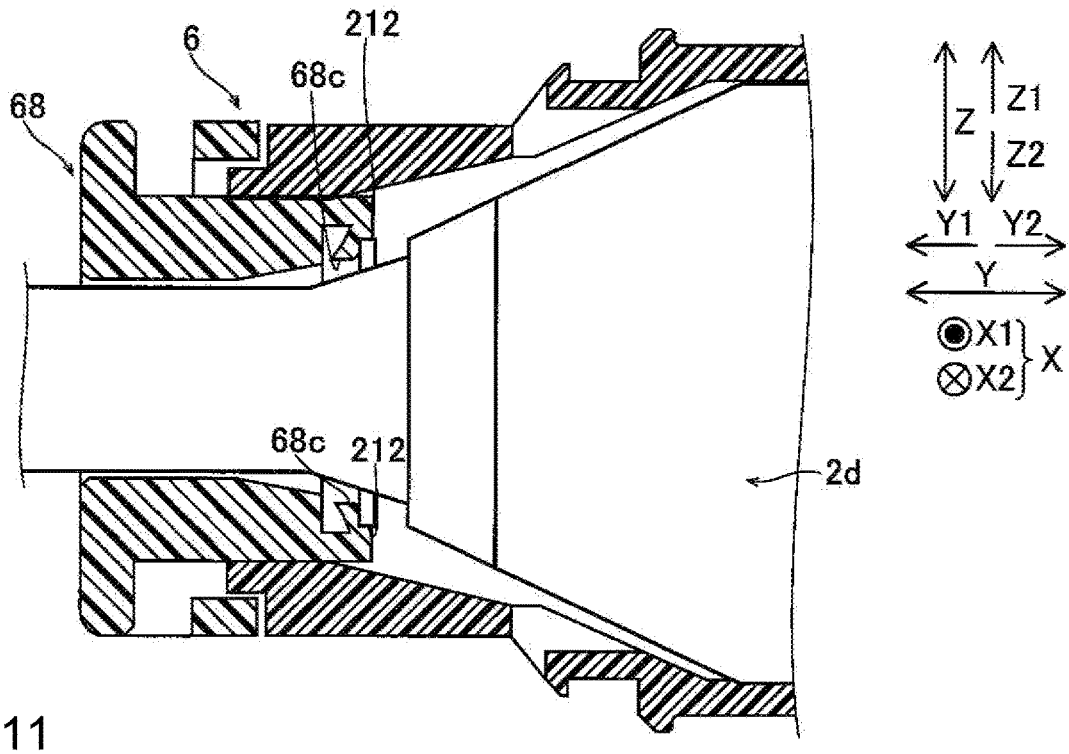
FIG. 10 is a diagram illustrating a cross sectional view of the endoscope adaptor according to a first embodiment, illustrating a state where a holder-side protrusion is elastically deformed by an endoscope-side protrusion from the Y2 side.
Figure 11:
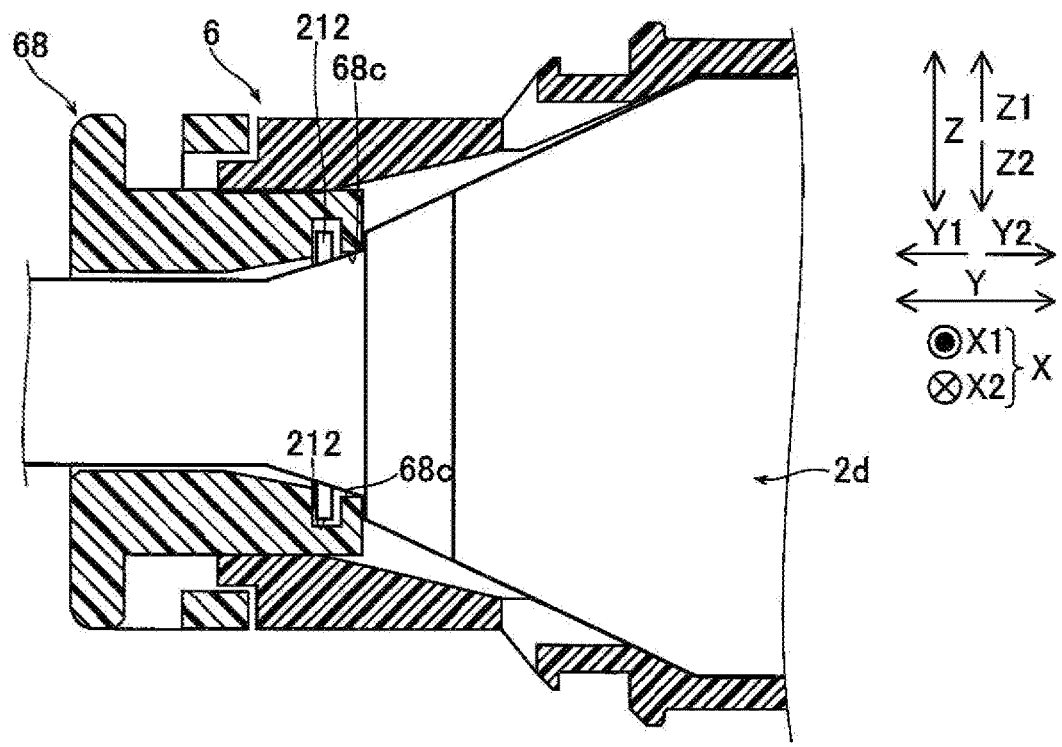
FIG. 11 is a diagram illustrating a cross sectional view of the endoscope adaptor according to a first embodiment, illustrating a state where the holder-side protrusion is engaged with the endoscope-side protrusion.
Figure 12:
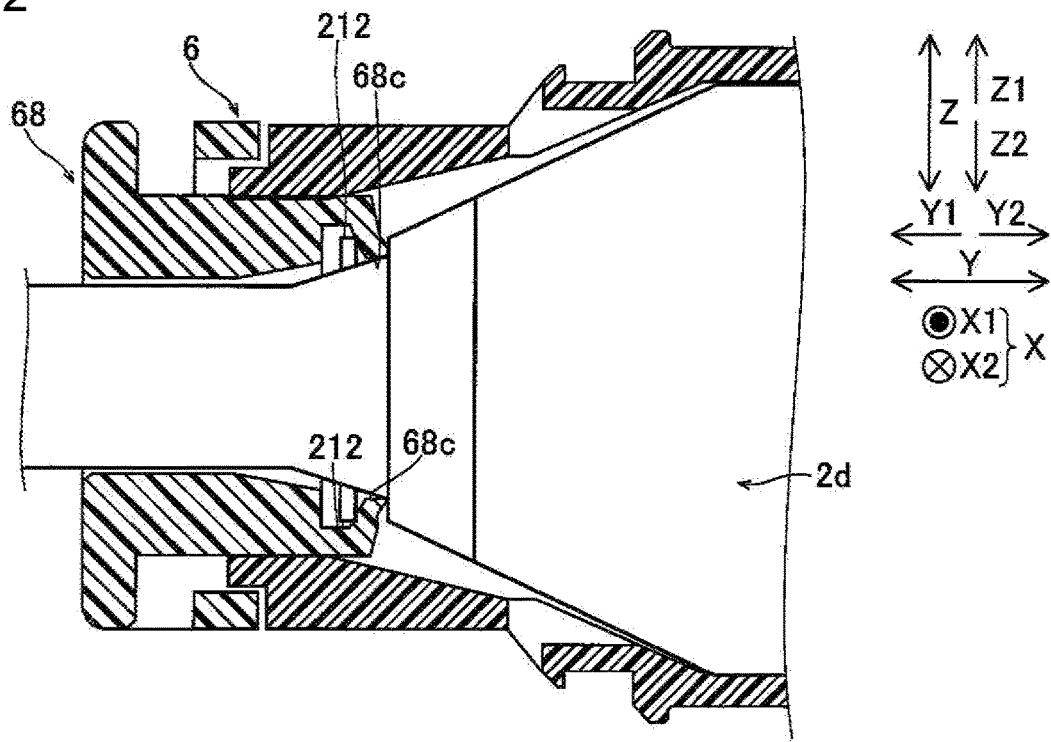
FIG. 12 is a diagram illustrating a cross sectional view of the endoscope adaptor according to a first embodiment, illustrating a state where the holder-side protrusion is elastically deformed by the endoscope-side protrusion from the Y1 side.

As illustrated in FIGS. 9 and 10, upon inserting the endoscope 2d, the endoscope-side protrusion 212 abuts on the holder-side protrusion 68c from the Y2 side and thus the holder-side protrusion 68c is elastically deformed toward the Y1 side. Then, when the holder-side protrusion 68c moves over the endoscope-side protrusion 212 and is engaged with the endoscope-side protrusion 212, the holder-side protrusion 68c hits the endoscope 2d so as to generate a sound. Further, as illustrated in FIGS. 11 and 12, upon removing the endoscope 2d from the endoscope holder 61, the endoscope-side protrusion 212 abuts the holder-side protrusion 68c from the Y1 side and thus the holder-side protrusion 68c is elastically deformed toward the Y2 side. Then, when the holder-side protrusion 68c moves over the endoscope-side protrusion 212 to be disengaged from the endoscope-side protrusion 212, the holder-side protrusion 68c hits the endoscope 2d so as to generate a sound.

Figure 13:
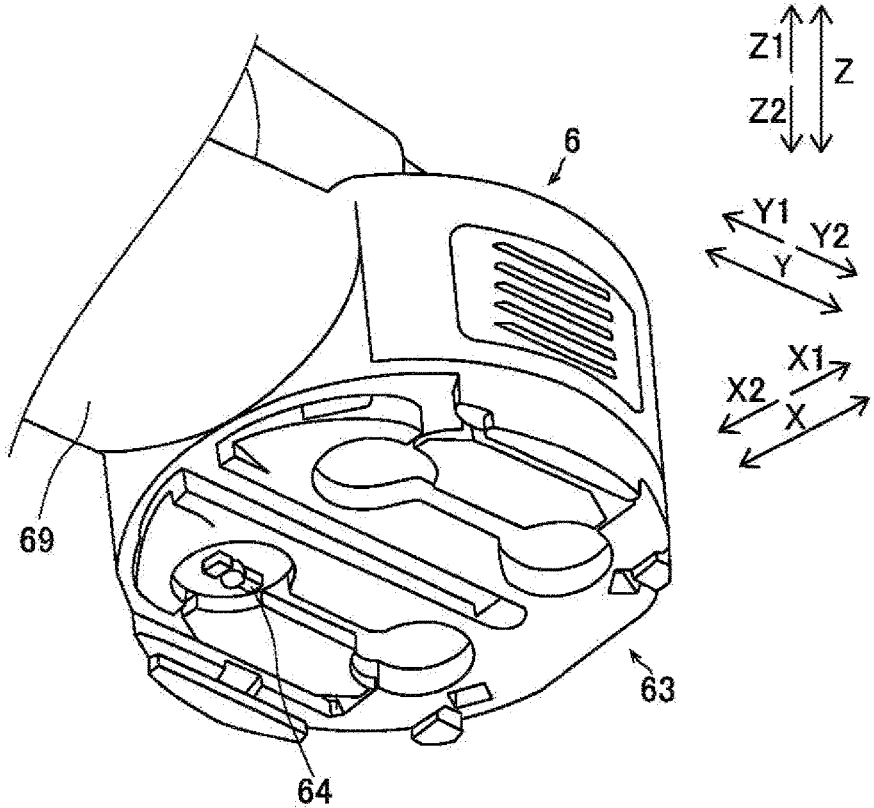
FIG. 13 is a diagram illustrating a perspective view of an attachment portion of the endoscope adaptor according to a first embodiment.
Figure 14:
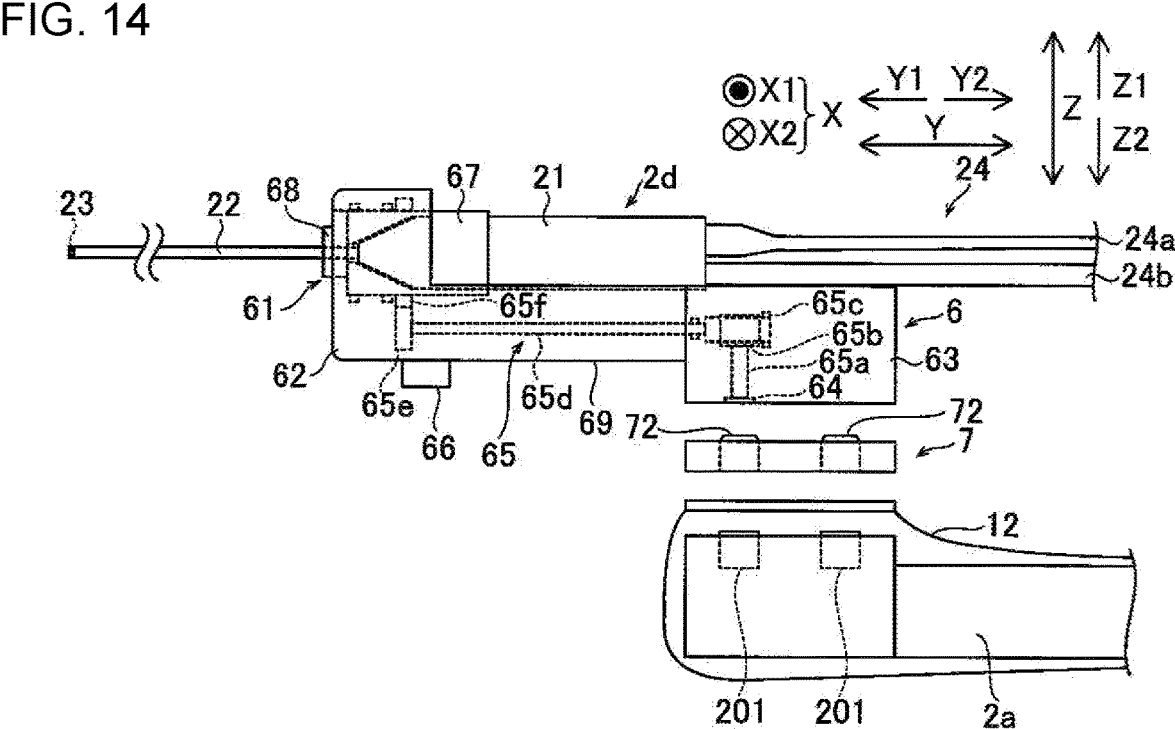
FIG. 14 is a diagram illustrating a side view of a transmission mechanism of the endoscope adaptor according to a first embodiment.

As illustrated in FIGS. 13 and 14, the attachment portion 63 is provided to detachably connect the endoscope adaptor 6 and the adaptor 7. The attachment portion 63 is provided on the Y2 side in the base portion 62. The attachment portion 63 includes an extension portion 69 extending in the Y1 direction. The driven member 64 is provided to the attachment portion 63.

The driven member 64 of the endoscope adaptor 6 are driven to be rotated so as to rotate the endoscope 2d. The number of the driven member 64 provided in the attachment portion 63 is one. The number of the rotational drive parts 201 provided in the robot arm 2a is four. Also, the number of the drive transmission members 72, to be engaged with the rotational drive parts 201, provided in the adaptor 7 is four. The rotational drive parts 201 of the robot arm 2a are engaged with the drive transmission members 72 of the adaptor 7. The drive transmission member 72 of the adaptor 7 is engaged with the driven member 64 of the endoscope adaptor 6. Therefore, the driven member 64 is driven to rotate by the rotational drive part 201 of the robot arm 2a via the adaptor 7.

The transmission mechanism 65 is configured to transmit the rotation of the driven member 64 to the endoscope holder 61 to rotate the endoscope 2d about the rotation axis C1 (see FIG. 5). The transmission mechanism 65 includes a shaft 65a, a helical tooth gear 65b, a cylindrical worm 65c, a shaft 65d, a gear 65e, and a gear 65f. The shaft 65a is connected to the helical tooth gear 65b. The helical tooth gear 65b is connected to (meshed with) the cylindrical worm 65c. The shaft 65d is connected to the gear 65e. The gear 65e is connected to (meshed with) the gear 65f. The gear 65f is connected to the endoscope holder 61. With this, by the rotation of the rotational drive part 201 of the robot arm 2a, the endoscope holder 61 is rotated and thus the endoscope 2d is rotated.

(Cable Holder)

Figure 15:
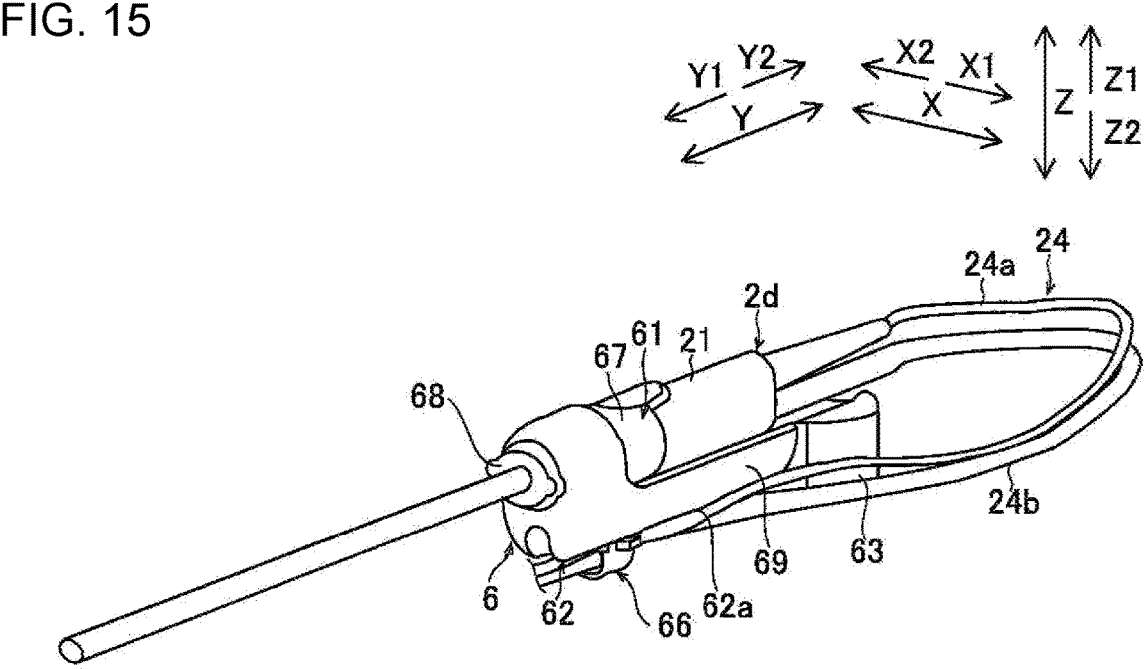
FIG. 15 is a diagram illustrating a perspective view of a state where the endoscope is attached to the endoscope adaptor according to a first embodiment.
Figure 16:
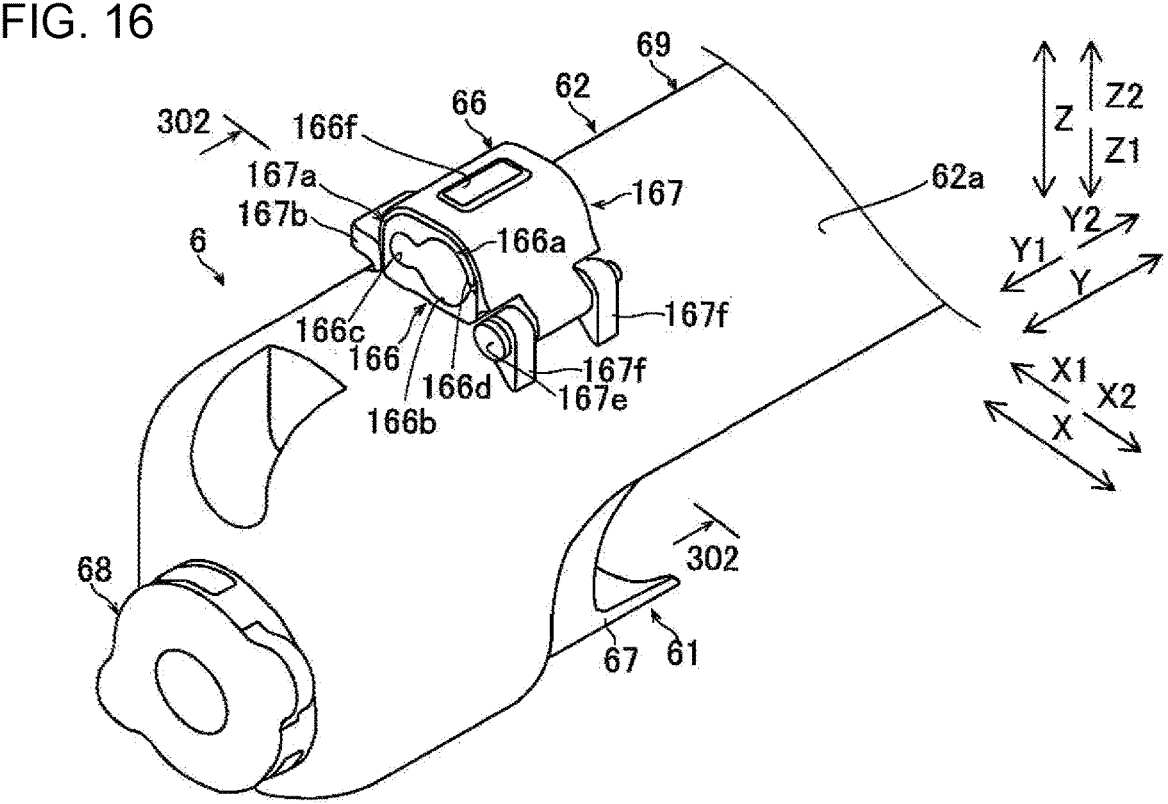
FIG. 16 is a diagram illustrating a perspective view of the endoscope adaptor according to a first embodiment as viewed from the Z2 side.

As illustrated in FIGS. 15 and 16, the cable holder 66 is configured as a clump mechanism that holds the cables 24 therein. That is, the cable holder 66 holds the cables 24 to arrange the cables 24 at a desired arrangement position.

The cable holder 66 is provided on a surface 62a of the base portion 62 that faces away from the endoscope 2d side in the Z direction (the direction in which the rotation axis C4 of the driven member 64 extends).

Accordingly, unlike a case where a cable holder is provided on a surface of the base portion 62 on the endoscope 2d side, the cables 24 connected to the endoscope 2d can be held along a direction in which the cables 24 hang down. Therefore, the cables 24 can be easily held by the cable holder 66.

Specifically, the cable holder 66 is attached to the Z2 side surface 62a of the extension portion 69. The cable holder 66 is disposed in a portion of the extension portion 69 on the Y1 side. That is, the cable holder 66 is arranged at a portion of the base portion 62 on the Z2 side with respect to the endoscope holder 61. The cable holder 66 is protruded from the surface 62a of the extension portion 69 on the Z2 side. The cable holder 66 is adjacent to the base portion 62 in the Z direction. The cable holder 66 extends in the X direction.

Figure 17:
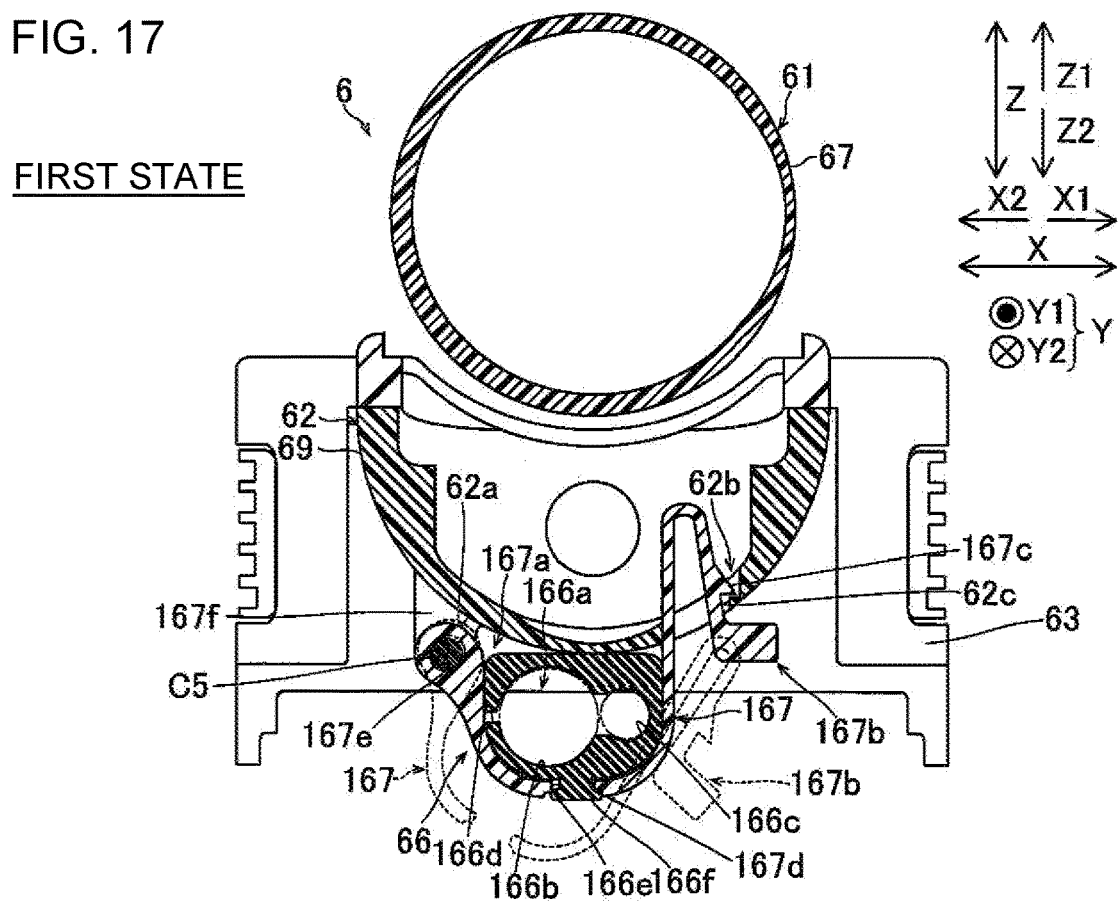
FIG. 17 is a diagram of a cross sectional view taken along the 302-302 line in FIG. 16, illustrating a first state where a holding member of the endoscope adaptor is closed according to a first embodiment.

As illustrated in FIGS. 16 and 17, the cable holder 66 includes an elastic member 166 to hold the cables 24.

Accordingly, the cables 24 can be held by the elastic member 166, which is a soft member having elasticity, so that the cables 24 can be protected from being excessively loaded.

The elastic member 166 is, for example, a silicone rubber. The elastic member 166 covers the cables 24 by being elastically deformed. The elastic member 166 has a function of protecting the cables 24 by covering the cables 24. That is, the elastic member 166 is a cushioning member for the cables 24 clamped by the cable holder 66. The elastic member 166 has a function of suppressing the deviation of the cables 24 in the Y direction due to the frictional resistance between the elastic member 166 and the cables 24. The elastic member 166 may be a member made of another material having elasticity instead of a silicon rubber.

The elastic member 166 has a through hole 166a that penetrates the elastic member 166. The through hole 166a has a light hole portion 166b into which a light cable 24b connected to the endoscope 2d is inserted. The through hole 166a has a camera hole portion 166c in which a camera cable 24a connected to the endoscope 2d is inserted. The camera hole portion 166c has a diameter smaller than that of the light hole portion 166b.

As a result, the camera cable 24a and the light cable 24b can be appropriately held by the light hole portion 166b and the camera hole portion 166c having diameters corresponding to the diameters of the camera cable 24a and the light cable 24b in the elastic member 166. Therefore, it is possible to suppress the complication of the structure of the elastic member 166.

The light hole portion 166b has a diameter that matches the diameter of the light cable 24b. Specifically, the light hole portion 166b has the diameter slightly smaller than the diameter of the light cable 24b. The light hole portion 166b penetrates the elastic member 166 in the Y direction. The camera hole portion 166c has a diameter that matches the diameter of the camera cable 24a. Specifically, the camera hole portion 166c has the diameter slightly smaller than the diameter of the camera cable 24a. The camera hole portion 166c penetrates the elastic member 166 in the Y direction. The light hole portion 166b and the camera hole portion 166c communicate with each other in the X direction.

The elastic member 166 includes a dividing portion 166d extending in a direction along the Y direction (the longitudinal direction of the base portion 62), in such a manner that the dividing portion 166d divides the through hole 166a in the X direction orthogonal to the Z direction (the direction of the rotation axis C4 (see FIG. 5) of the driven member 64) and the Y direction (the longitudinal direction of the base portion 62). The through hole 166a is configured to be openable and closable by the dividing portion 166d of the elastic member 166.

Accordingly, the cable 24 can be attached to and removed from the through hole 166a in the state where the through hole 166a is opened from the dividing portion 166d, whereas the cable 24 can be held in the through hole 166a in the state the through hole 166a is closed at the dividing portion 166d. Therefore, both the removal of the cable 24 from the through hole 166a and the attachment of the cable 24 into the through hole 166a can be easily performed.

The dividing portion 166d is a minute gap formed in the elastic member 166 in the Y direction. The dividing portion 166d divides an end portion of the elastic member 166 on the X2 side. With this, the through hole 166a is configured to open the light hole portion 166b and the camera hole portion 166c, by moving the end portion of the elastic member 166 on the divided portion 166d side about the X1 side end portion of the elastic member 166.

Figure 18:
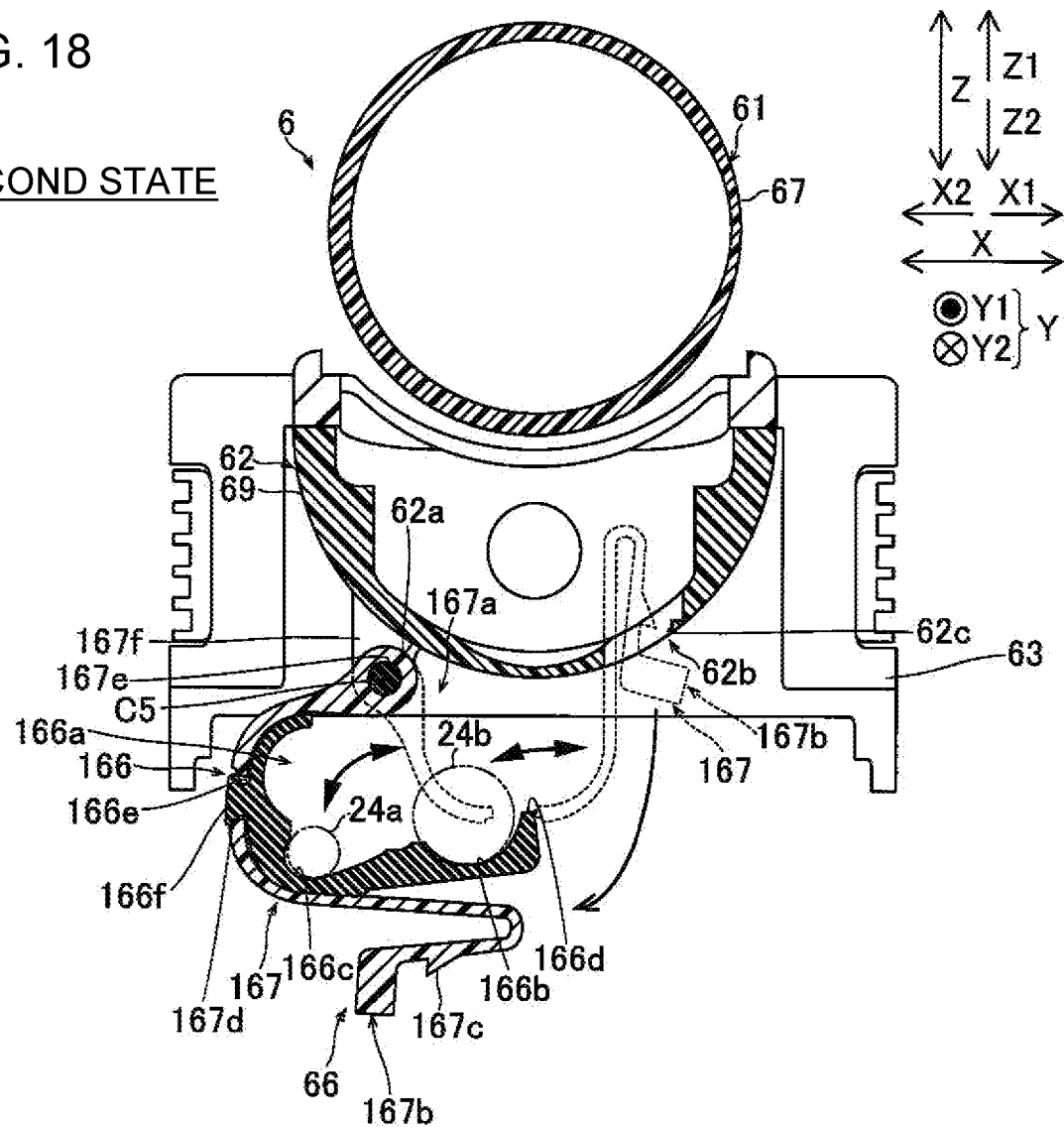
FIG. 18 is a diagram of a cross sectional view taken along the 302-302 line in FIG. 16, illustrating a second state where the holding member of the endoscope adaptor is opened according to a first embodiment.

The cable holder 66 includes a holding member 167 that can switch between a first state (see FIG. 17) in which the holding member 167 is engaged with the base portion 62 while holding the elastic member 166 and a second state (see FIG. 18) in which the holding member 167 is disengaged from the base portion 62 while holding the elastic member 166.

Accordingly, the holding member 167 can switch between the first state and the second state while maintaining the state in which the elastic member 166 is held. Thus, upon switching between the first state and the second state, it is possible to prevent the elastic member 166 that holds the cables 24 from coming off from the holding member 167, so as to prevent the cables 24 from falling to the floor.

The holding member 167 is made of resin. The holding member 167 covers the elastic member 166 arranged in the holding member 167. The holding member 167 is in contact with the outer surface of the elastic member 166 on the Z2 side. The holding member 167 supports the elastic member 166 from the Z2 side. In the first state, the holding member 167 is configured to accommodate the elastic member 166 in an accommodation space 167a between the elastic member 166 and the Z2 side surface 62a of the base portion 62. The holding member 167 presses the elastic member 166 against the Z2 side surface 62a of the base portion 62 in the state of accommodating the elastic member 166 in the accommodation space 167a. As a result, the elastic member 166 is compressed. In the second state, the holding member 167 is configured to release the elastic member 166 from the state of accommodating the elastic member 166 in the accommodation space 167a. Accordingly, the elastic member 166 can be released from the accommodation space 167a, so that the elastic member 166 can be taken out from the holding member 167. That is, it is possible to rotate the end portion of the elastic member 166 on the divided portion 166d side.

The holding member 167 is attached to the base portion 62 so as to be rotatable with respect to the base portion 62 about a rotation axis C5 extending in parallel with the Y direction (the longitudinal direction of the base portion 62). The holding member 167 includes an elastically deformable portion 167b which is engaged with the base portion 62 in the first state by being elastically deformed when the holding member 167 is rotated toward the base portion 62 and is disengaged from the base portion 62 in the second state by being elastically deformed.

Accordingly, the holding member 167 can be attached to and detached from the base portion 62 with the elastically deformable portion 167b only by elastically deforming the elastically deformable portion 167b, so that the holding member 167 can be easily attached to and detached from the base portion 62.

The elastically deformable portion 167b is configured to be elastically deformable in a direction approaching the elastic member 166. That is, upon inserting the elastically deformable portion 167b into the attachment hole 62b formed in the base portion 62, the elastically deformable portion 167b is elastically deformed in a direction approaching the elastic member 166 (see the dotted line in FIG. 17) so that the elastically deformable portion 167b can be contracted in the direction approaching the elastic member 166. With this, the elastically deformable portion 167b can be inserted into the attachment hole 62b. Further, upon taking out the elastically deformable portion 167b from the attachment hole 62b, the elastically deformable portion 167b is elastically deformed in the direction approaching the elastic member 166 (see the dotted line in FIG. 18), so that the elastically deformable portion 167b can be contracted in the direction approaching the elastic member 166. Accordingly, the elastically deformable portion 167b can be taken out from the inside of the attachment hole 62b.

The elastically deformable portion 167b has a claw portion 167c that is engaged with a protrusion 62c of the attachment hole 62b. The protrusion 62c of the attachment hole 62b protrudes from the inner surface of the attachment hole 62b on the X1 side toward the X2 direction. The claw portion 167c protrudes from an outer surface of the elastically deformable portion 167b that faces the claw portion 167c in a direction opposite to the projecting direction of the protrusion 62c. In the first state, the claw portion 167c and the protrusion 62c overlap each other when viewed from the Z2 side. The engaged state in which the claw portion 167c and the protrusion 62c are engaged is released by contracting the elastically deformable portion 167b in the direction of approaching the elastic member 166.

As illustrated in FIGS. 16 and 17, the holding member 167 is provided with a rotation shaft 167e for rotating the holding member 167 about the rotation axis C5 extending parallel to the Y direction (the longitudinal direction of the base portion 62). The holding member 167 includes a support portion 167f that is protruded from the base portion 62 and supports the rotation shaft 167e.

Accordingly, since the structure for rotating the holding member 167 while holding the elastic member 166 can be realized by a simple structure, it is possible to prevent the structure of the cable holder 66 from becoming complicated.

The holding member 167 is composed of a hinge structure including the rotation shaft 167e and the support portion 167f. The rotation shaft 167e is a metal pin extending in the Y direction. The rotation shaft 167e is provided on the X2 side of the holding member 167. The support portion 167f protrudes in the Z2 direction from the Z2 side surface 62a of the base portion 62. A plurality (two) of the support portions 167f are arranged in the Y direction. The plurality of the support portions 167f supports the Y1 side end portion of the rotation shaft 167e and the Y2 side end portion of the rotation shaft 167e.

The elastic member 166 is detachably attached to the holding member 167.

Accordingly, the elastic member 166 can be easily replaced, so that the elastic member 166 can appropriately protect the cables 24.

The elastic member 166 is engaged with the holding member 167. Specifically, the holding member 167 is formed with an engagement hole 167d. The engagement hole 167d penetrates the holding member 167 in the Y direction. The engagement hole 167d is an elongated hole extending in the Y direction. The elastic member 166 includes a reduced portion 166e, which is to be disposed in the engagement hole 167d in a state of being attached to the holding member 167. The elastic member 166 includes an enlarged portion 166f, which is to be engaged with an edge portion of the engagement hole 167d on the Z2 side in the state of being attached to the holding member 167. The size (dimensions) of the enlarged portion 166f is larger than the size (dimensions) of the reduced portion 166e. Further, in the direction orthogonal to the Z direction, the size (dimension) of the enlarged portion 166f is larger than the size (dimension) of the engagement hole 167d. Accordingly, the enlarged portion 166f is elastically deformed, so that the reduced portion 166e is inserted into the engagement hole 167d. Then, the enlarged portion 166f of the elastic member 166 and the engagement hole 167d of the holding member 167 are engaged with each other. In this way, the elastic member 166 is attached to the holding member 167.

Second Embodiment

With reference to FIGS. 1 to 3 and 19 to 24, a configuration of an endoscope adaptor 606 according to a second embodiment is described. In a second embodiment, unlike a first embodiment, a rotation prevention member 762 for preventing an unintended rotation of a shaft 65d is provided in a base portion 62. In a second embodiment, the description of the same configuration as that in a first embodiment may be omitted.

As illustrated in FIGS. 1 to 3, a robotic surgical system 100 includes a remote control apparatus 1, a patient-side apparatus 2, and an image processing apparatus 3. In response to an action mode instruction transmitted from the remote control apparatus 1, the patient-side apparatus 2 operates an endoscope 2d attached to a robot arm 2a.

Figure 19:
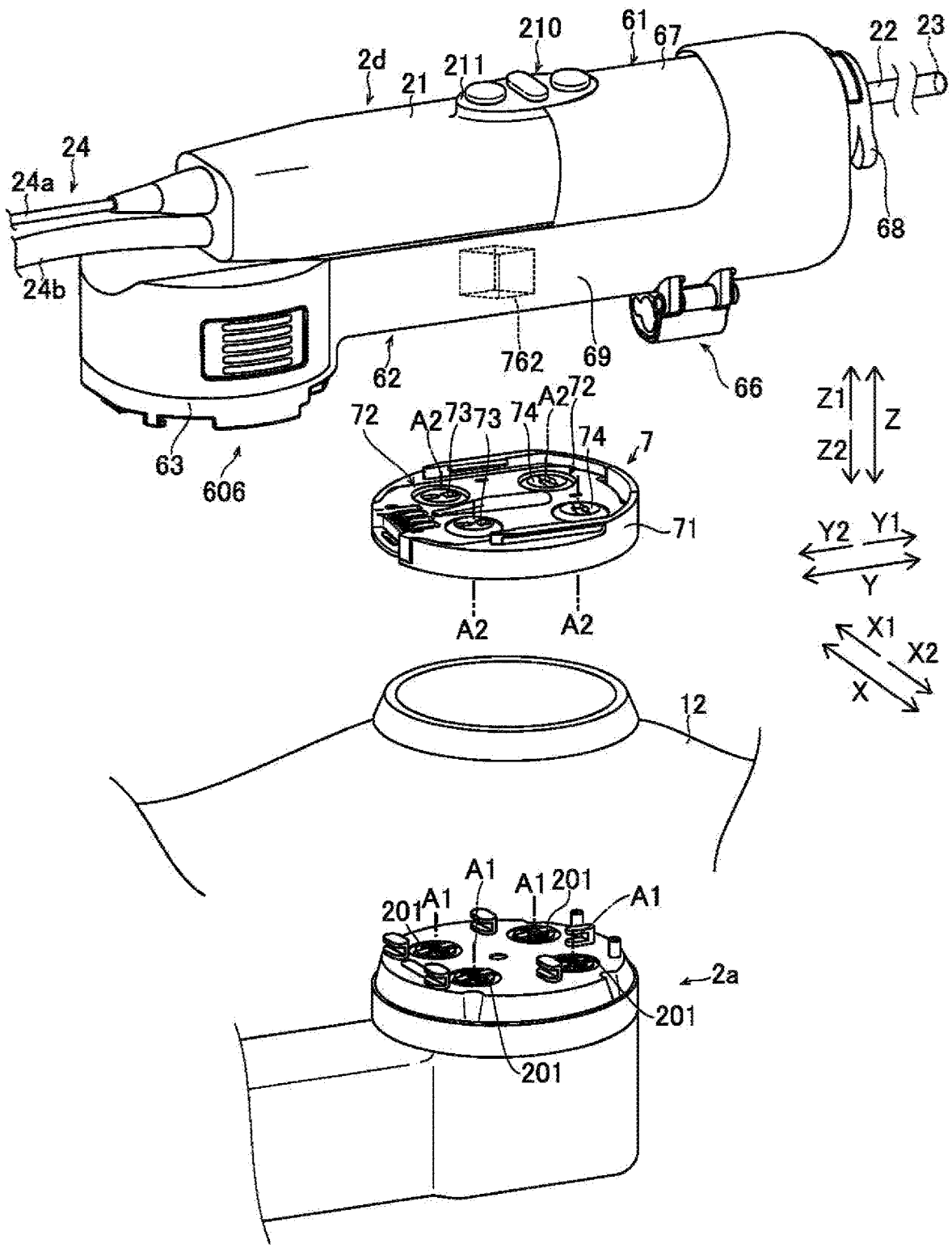
FIG. 19 is a diagram illustrating an exploded perspective view of a state where an adaptor and an endoscope adaptor are detached from a robot arm according to a second embodiment.

As illustrated in FIG. 19, in a state where the endoscope adaptor 606 is attached to the endoscope 2d, the endoscope 2d is connected to the robot arm 2a of the robotic surgical system 100 through an adaptor 7. The robot arm 2a transmits driving force to the endoscope adaptor 606 through the adaptor 7 to rotate the endoscope 2d. Specifically, the robot arm 2a is provided with rotational drive parts 201. The rotational drive part 201 is configured to be rotated about a rotation axis A1 extending in the Z direction by means of a drive source such as a motor or the like. Note that rotational drive part 201 is an example of a drive part.

The adaptor 7 includes a base body 71 and plural drive transmission members 72. The drive transmission members 72 include first drive transmission members 73 arranged in the Y2 side and second drive transmission members 74 arranged in the Y1 side. The drive transmission members 72 are rotatably provided in the base body 71. Specifically, the drive transmission members 72 are provided to be rotatable about rotation axes A2 extending in the Z direction. The drive transmission member 72 transmits driving force of the rotational drive part 201 of the robot arm 2a to a driven member 64 of the endoscope adaptor 606.

(Endoscope Adaptor)

Figure 20:
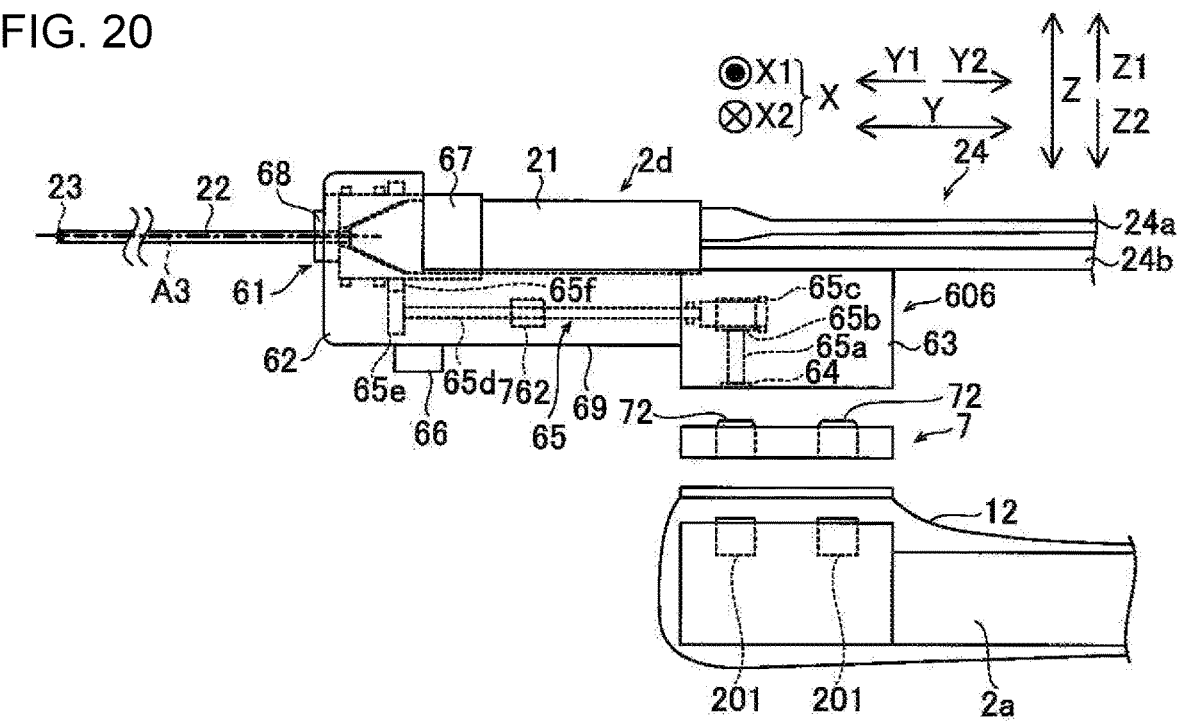
FIG. 20 is a diagram illustrating a side view of a transmission mechanism of the endoscope adaptor according to a second embodiment.
Figure 21:
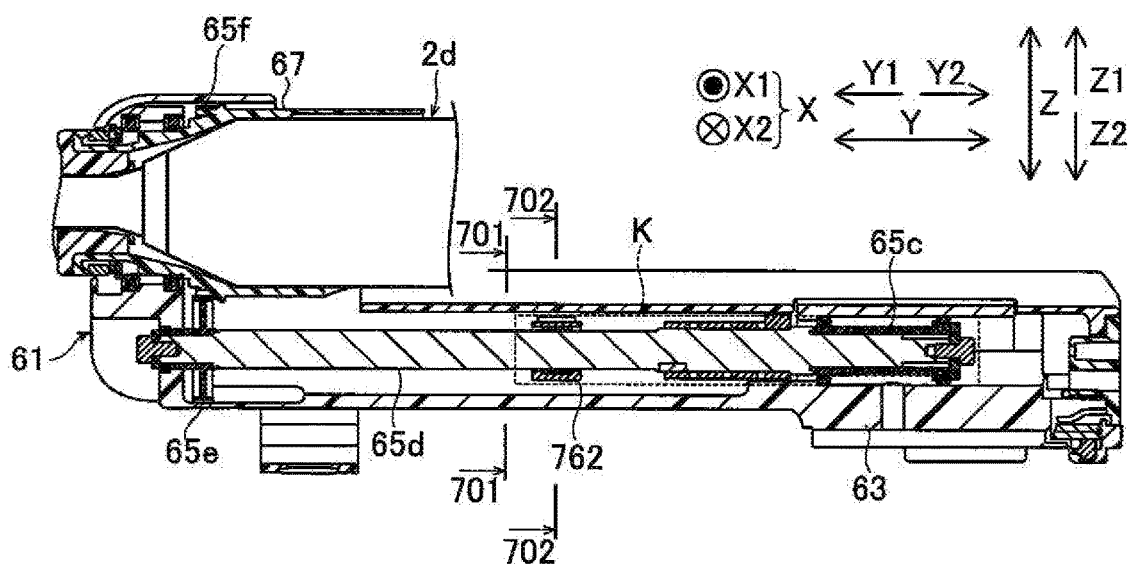
FIG. 21 is a diagram illustrating a cross sectional view of the endoscope adaptor along an extending direction of a shaft according to a second embodiment.

As illustrated in FIGS. 20 and 21, the endoscope adaptor 606 includes an endoscope holder 61, a base portion 62, an attachment portion 63, the driven member 64, a transmission mechanism 65, and a cable holder 66.

The endoscope holder 61 is configured to hold the endoscope 2d that is inserted in the endoscope holder 61. That is, the endoscope holder 61 is configured to attach the endoscope 2d to the base portion 62. Specifically, the endoscope holder 61 includes a holder main body 67 and a lock part 68.

The holder main body 67 has a substantially circular cylindrical shape. The holder main body 67 includes an insertion hole 67a to which the endoscope 2d is to be inserted. The insertion hole 67a penetrates through the holder main body 67 in the Y direction.

The attachment portion 63 is provided to detachably connect the endoscope adaptor 606 and the adaptor 7. The attachment portion 63 is provided on the Y2 side in the base portion 62 The attachment portion 63 includes an extension portion 69 extending in the Y1 direction. The driven member 64 is provided to the attachment portion 63.

The driven member 64 of the endoscope adaptor 606 is driven to be rotated so as to rotate the endoscope 2d. The rotational drive parts 201 of the robot arm 2a are engaged with the drive transmission members 72 of the adaptor 7. The drive transmission member 72 of the adaptor 7 is engaged with the driven member 64 of the endoscope adaptor 606. Therefore, the driven member 64 is driven to rotate by the rotational drive part 201 of the robot arm 2a via the adaptor 7.

The transmission mechanism 65 is configured to transmit the rotation of the driven member 64 to the endoscope holder 61 to rotate the endoscope 2d about the rotation axis A3. The transmission mechanism 65 includes a shaft 65a, a helical tooth gear 65b, a cylindrical worm 65c, a shaft 65d, a gear 65e, and a gear 65f. Note that the gear 65f is an example of a first gear. The helical tooth gear 65b is an example of a second gear. The gear 65e is an example of a third gear. The cylindrical worm 65c is an example of a fourth gear. The shaft 65d is an example of a drive transmission shaft.

The shaft 65a is connected to the helical tooth gear 65b. The helical tooth gear 65b is connected to (meshed with) the cylindrical worm 65c. The shaft 65d is connected to the gear 65e. The gear 65e is connected to (meshed with) the gear 65f. The gear 65f is connected to the endoscope holder 61. With this, by the rotation of the rotational drive part 201 of the robot arm 2a, the endoscope holder 61 is rotated and thus the endoscope 2d is rotated.

The cable holder 66 is configured as a clump mechanism that holds the cables 24 therein. That is, the cable holder 66 holds the cables 24 to arrange the cables 24 at a desired arrangement position.

(Rotation Prevention Member)

Figure 22:
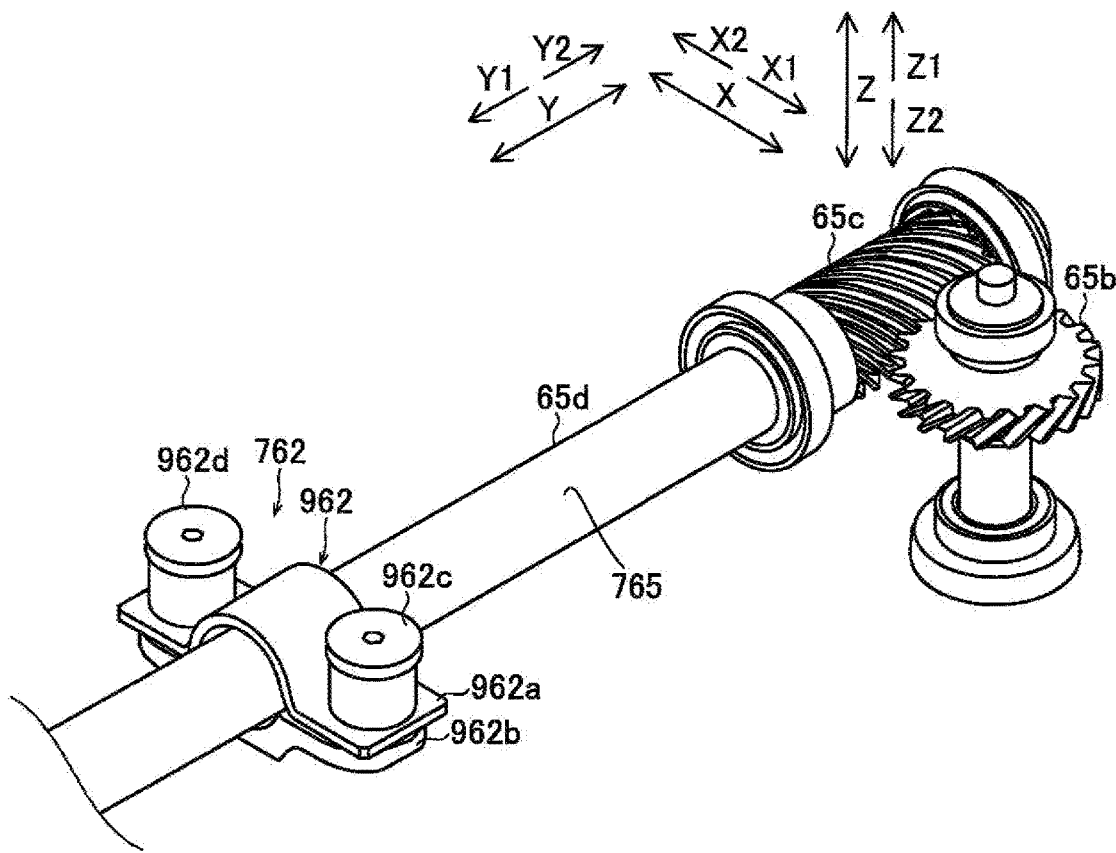
FIG. 22 is a diagram illustrating an enlarged perspective view of the K part in FIG. 21.

As illustrated in FIGS. 21 and 22, the endoscope adaptor 606 according to a second embodiment is configured to brake the rotation of the endoscope 2d when the rotational drive part 201 of the robot arm 2a is not driven, in order not to change the field of view of the endoscope 2d during the surgery unintentionally. It may be a problem that the endoscope 2d unintentionally rotates when an external force is applied to the cable 24 by an operator or an assistant touching the cable 24. Therefore, the endoscope adaptor 606 according to a second embodiment is configured to brake the endoscope 2d so that the endoscope 2d does not rotate unintentionally.

That is, the endoscope adaptor 606 is configured such that the position of the endoscope 2d can be fixed when the rotational drive part 201 of the robot arm 2a is not driven.

Specifically, the gear 65f is connected to the endoscope holder 61. The helical tooth gear 65b is connected to the driven member 64. The transmission mechanism 65 includes the gear 65e that meshes with the gear 65f, the cylindrical worm 65c that meshes with the helical tooth gear 65b, and the shaft 65d to which the gear 65e and the cylindrical worm 65c are connected and which is rotated by rotation of the driven member 64. The base portion 62 includes the rotation prevention member 762 configured to prevent the rotation of the endoscope holder 61 when the driven member 64 is not rotationally driven by the rotational drive part 201 of the robot arm 2a.

As a result, the rotation of the endoscope holder 61 due to an external force, such as an operator or an assistant touching the cable 24, can be prevented (suppressed) by the rotation prevention member 762, so that an unintended change of the field of view of the endoscope 2d can be prevented (suppressed).

Figure 23:
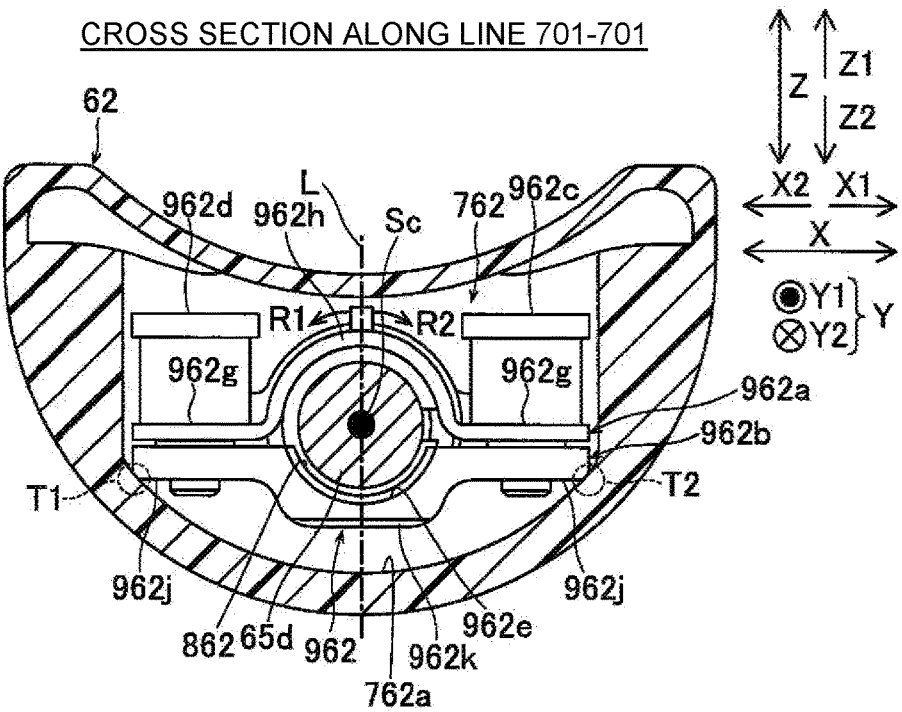
FIG. 23 is a diagram illustrating a cross sectional view taken along the 701-701 line in FIG. 21.
Figure 24:
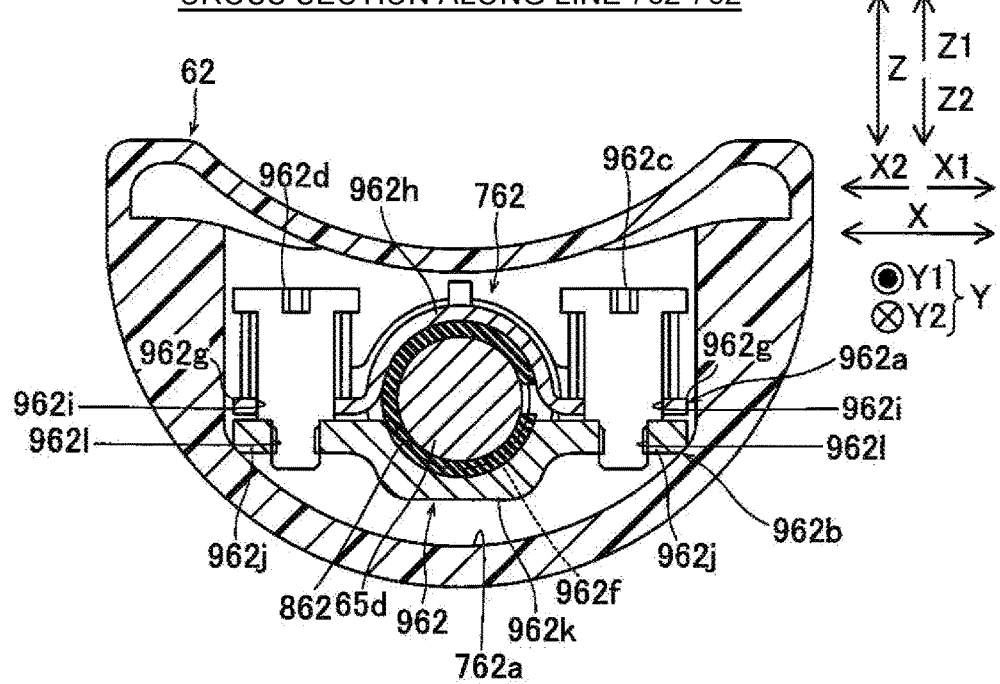
FIG. 24 is a diagram illustrating a cross-sectional view taken along the 702-702 line in FIG. 21.

As illustrated in FIGS. 23 and 24, the rotation prevention member 762 is configured to contact with the shaft 65d to prevent the rotation of the shaft 65d so as to prevent the rotation of the endoscope holder 61.

Accordingly, unlike a case where the rotation prevention member 762 is in direct contact with the endoscope holder 61 to prevent (suppress) the rotation of the endoscope holder 61, the rotation prevention member 762 can be provided at a position where the rotation prevention member 762 does not hinder the insertion of the endoscope 2d into the endoscope holder 61. As a result, the endoscope 2d can be easily attached to the endoscope holder 61, and an unintended change in the field of view of the endoscope 2d can be prevented.

That is, the rotation prevention member 762 is configured to prevent the shaft 65d from rotating when the torque applied to the shaft 65d is smaller than a predetermined torque when the driven member 64 is not rotationally driven by the rotational drive part 201 of the robot arm 2a. Further, the rotation prevention member 762 is configured to allow the shaft 65d to rotate with respect to the rotation prevention member 762, when the driven member 64 is rotationally driven by the rotational drive part 201 of the robot arm 2a and thus the torque equal to or higher than the predetermined torque is applied to the shaft 65d.

According to this configuration, since the rotation prevention member 762 is configured to prevent the shaft 65d from rotating when the torque applied to the shaft 65d is smaller than the predetermined torque, the rotation of the shaft 65d due to an external force, such as the operator or the assistant touching the cable 24, can be prevented (suppressed) by the rotation prevention member 762. Further, when the torque transmitted from the rotational drive part 201 of the robot arm 2a to the shaft 65d is equal to or more than the predetermined torque, the shaft 65d can be rotated. As a result, since the shaft 65d can be appropriately driven when the rotational drive part 201 of the robot arm 2a is driven, the field of view of the endoscope 2d can be appropriately changed when the rotational drive part 201 of the robot arm 2a is driven, while an unintended change of the field of view of the endoscope 2d can be appropriately prevented (suppressed) when the rotational drive part 201 of the robot arm 2a is not driven.

Here, the rotation prevention member 762 is configured to prevent the rotation of the shaft 65d due to friction between portions where the rotation prevention member 762 and the shaft 65d are in contact with each other, thereby preventing the rotation of the endoscope holder 61.

As a result, the rotation prevention member 762 can more reliably apply a load to the rotation of the shaft 65d, as compared with a case where the rotation of the shaft 65d is prevented by a non-contact method using electrostatic force or magnetic force. The rotation of the shaft 65d can be prevented (suppressed) more reliably.

Specifically, the shaft 65d is provided inside the base portion 62. The rotation prevention member 762 includes a braking part 862 that is in contact with an outer circumference of the shaft 65*d* as surrounding the outer circumference of the shaft 65*d*. The rotation prevention member 762 includes a holding portion 962 that is provided inside the base portion 62, holds the braking part 862, and abuts on an internal portion of the base portion 62.

As a result, it is possible to prevent (suppress) the holding portion 962 from rotating together with the shaft 65*d* without fixing the holding portion 962 to the base portion 62. Further, since the holding portion 962 is not fixed to the base portion 62, the rotation prevention member 762 can be easily assembled to the base portion 62.

The braking part 862 has a C-shape with a slit extending along the Y direction when viewed from the Y1 side (the axial direction of the shaft 65*d*). The braking part 862 is a rubber member. The braking part 862 is made of a silicone rubber. The braking part 862 is in contact with an outer circumferential surface 765 of the shaft 65*d* at a portion of the braking part 862 other than the slit. The braking part 862 stops the rotation of the shaft 65*d* due to the friction between the shaft 65*d* and the portion of the braking part 862 in contact with the shaft 65*d* when the torque applied to the shaft 65*d* is smaller than the predetermined torque. The braking part 862 may be made of a material other than the silicone rubber.

The holding portion 962 includes a first bracket 962*a*, a second bracket 962*b*, a first fastener 962*c*, a second fastener 962*d*, a first retaining portion 962*e*, and a second retaining portion 962*f*.

The first bracket 962*a* is arranged on the Z1 side (the endoscope holder 61 side) with respect to the shaft 65*d*. The first bracket 962*a* presses the shaft 65*d* from the Z1 side via the braking part 862. The second bracket 962*b* is arranged on the Z2 side (the attachment portion 63 side) with respect to the shaft 65*d*. The second bracket 962*b* presses the shaft 65*d* from the Z2 side via the braking part 862.

The first bracket 962*a* has a pair of first protruding portions 962*g* and a first connecting portion 962*h* having a semicircular cross section connecting the pair of first protruding portions 962*g*. The pair of first protruding portions 962*g* project outward in the radial directions of the shaft 65*d*. The pair of first protruding portions 962*g* are arranged line-symmetrically with respect to a virtual line L extending in the Z direction passing through the rotation axis Sc of the shaft 65*d* when viewed from the Y1 side. Each of the pair of first protruding portions 962*g* has a through hole 962*i*. The second bracket 962*b* has the same shape as the first bracket 962*a*, and includes a pair of second protruding portions 962*j* and a second connecting portion 962*k* having a semicircular cross section that connects the pair of second protruding portions 962*j*. The pair of second protruding portions 962*j* project outward in the radial directions of the shaft 65*d*. The pair of second protruding portions 962*j* are arranged line-symmetrically with respect to the virtual line L extending in the Z direction passing through the rotation axis Sc of the shaft 65*d* when viewed from the Y1 side. Each of the pair of second protruding portions 962*j* includes a female threaded portion 962*l*. The pair of second protruding portions 962*j* is an example of a pair of protruding portions.

The first fastener 962*c* is disposed on the X1 side with respect to the shaft 65*d*. The first fastener 962*c* is screwed into the female thread portion 962*l* of the second protruding portion 962*j* arranged on the X1 side in a state of being inserted into the through hole 962*i* of the first protruding portion 962*g* arranged on X1 side. The first fastener 962*c* and the X1-side second protruding portion 962*j* of the second bracket 962*b* sandwich therebetween the X1-side first protruding portion 962*g* of the first bracket 962*a*. The second fastener 242 is disposed on the X2 side with respect to the shaft 65*d*. The second fastener 962*d* is screwed into the female thread portion 962*l* of the second protruding portion 962*j* arranged on the X2 side in a state of being inserted into the through hole 962*i* of the first protruding portion 962*g* arranged on the X2 side. The second fastener 962*d* and the X2-side second protruding portion 962*j* of the second bracket 962*b* sandwich therebetween the X2-side first protruding portion 962*g* of the first bracket 962*a*.

The rotation prevention member 762 is attached to the shaft 65*d* by fastening the first bracket 962*a* and the second bracket 962*b* by the first fastener 962*c* and the second fastener 962*d* in such a manner that the shaft 65*d* is sandwiched between the first bracket 962*a* and the second bracket 962*b*.

Further, the base portion 62 includes an inner surface 762*a* facing the shaft 65*d*. The holding portion 962 includes a pair of second protruding portions 962*j* that project outward in the radial directions of the shaft 65*d*. The holding portion 962 has the pair of second protruding portions 962*j* in contact with the inner surface 762*a* of the base portion 62.

Accordingly, such a simple structure can prevent the holding portion 962 from rotating together with the rotation of the shaft 65*d*. Therefore, it is possible to suppress the complexity of the structure of the rotation prevention member 762.

Specifically, with respect to the rotation of the holding portion 962 about the shaft 65*d* in one direction (R1 direction), one of the pair of second protruding portions 962*j* on the X2 side (one side) abuts on a portion (the T1 portion in FIG. 23) of the inner surface 762*a* of the base portion 62 on the Z2 side (on the attachment portion 63 side). With this, the rotation of the holding portion 962 in the R1 direction is restricted. On the other hand, with respect to the rotation of the holding portion 962 about the shaft 65*d* in the other direction (R2 direction), the other of the pair of second protruding portions 962*j* on the X1 side (the other side) abuts on a portion (the T2 portion in FIG. 23) of the inner surface 762*a* of the base portion 62 on the Z2 side (the attachment portion 63 side). With this, the rotation of the holding portion 962 in the R2 direction is restricted.

The first retaining portion 962*e* is provided on the Y1 side of the second bracket 962*b* in order to prevent the braking part 862 from coming off toward the Y1 side. The first retaining portion 962*e* is protruded from a Z1 side surface of the second bracket 962*b* toward the Z1 side. The first retaining portion 962*e* is overlapped, in the Y direction, with a portion of the braking part 862 on the Z2 side. The second retaining portion 962*f* is provided on the Y2 side of the second bracket 962*b* in order to prevent the braking part 862 from coming off toward the Y2 side. The second retaining portion 962*f* is protruded from a Z1 side surface of the second bracket 962*b* toward the Z1 side. The second retaining portion 962*f* is overlapped, in the Y direction, with a portion of the braking part 862 on the Z2 side.

(Modifications)

It should be understood that first and second embodiments described above are illustrated by way of example in every respect and do not limit the disclosure. The scope of the invention is indicated by claims and includes equivalents to the claims and all alterations (modification) within the same.

For example, in first and second embodiments described above, the case has been described in which the cable holder 66 includes the elastic member 166 in order to hold the cables 24. However, the invention is not limited thereto. In the invention, a cable holder may use a member other than an elastic member that does not elastically deform, as a member for holding a cable.

Also, in first and second embodiments described above, the case has been described in which the through hole 166*a* includes the light hole portion 166*b* and the camera hole portion 166*c*. However, the invention is not limited to this. In the invention, a through hole may include a hole corresponding to a cable dedicated to power supply connected to the endoscope, other than or in addition to the light hole portion and the camera hole portion.

Also, in first and second embodiments described above, the case has been described in which the engagement portion 67*c* of the endoscope holder 61 is the notch 67*d*. However, the invention is not limited to this. In the invention, an engagement portion of an endoscope holder may have a structure other than the notch as long as it has a shape that matches a shape of an engagement portion of an endoscope.

Also, in first and second embodiments described above, the case has been described in which the notch 67*d* positions the endoscope 2*d* to the predetermined position 15 in the Y1 direction (the insertion direction) with the engagement portion 67*c* and the engagement portion 210 being engaged with each other. However, the invention is not limited thereto. In the invention, a notch may not position an endoscope to a predetermined position in an insertion direction of the endoscope in a state where an engagement portion of an endoscope holder and an engagement portion of the endoscope are engaged with each other.

Also, in first and second embodiments described above, the case has been described in which the holder-side protrusion 68*c* is configured to generate a sound upon engaging with and disengaging from the endoscope-side protrusion 212. However, the invention is not limited thereto. In the invention, a holding-side protrusion may be configured to generate no sound upon engaging with or disengaging an endoscope-side protrusion.

In first and second embodiments described above, the case has been described in which the cable holder 66 is provided on the surface 62*a* of the extension portion 69 of the base portion 62 that faces away from the endoscope 2*d* side in the Z direction. However, the invention is not limited to this. In the invention, a cable holder may be provided at another location, such as a surface of an attachment portion that faces away from an endoscope side in the direction of a rotation axis of a driven member.

Also, in first and second embodiments described above, the case has been described in which the holding member 167 is composed of the hinge structure including the rotation shaft 167*e* and the support portion 167*f*. However, the invention is not limited to this. In the invention, a holding member may be composed of a leaf spring that biases toward an outer surface of a base portion on a side of an attachment portion.

Also, in first and second embodiments described above, the case has been described in which the holding member 167 includes the elastically deformable portion 167*b*. However, the invention is not limited to this. In the invention, a holding member may not include an elastically deformable portion.

Also, in first and second embodiments described above, the case has been described in which the elastic member 166 is detachably attached to the holding member 167. However, the invention is not limited to this. In the invention, an elastic member may be fixed to a holding member with an adhesive or the like.

Also, in first and second embodiments described above, the case has been described in which only one driven member 64 is provided in the endoscope adaptor 6 or 606. However, the invention is not limited thereto. In the invention, two or more driven members may be provided in an endoscope adaptor.

Also, in first and second embodiments described above, the case has been described in which the common adaptor 7 (drape adaptor) is used for attaching the surgical instrument 2*c* to the robot arm 2*b* and for attaching the endoscope adaptor 6 or 606 to the robot arm 2*a*. However, the invention is not limited to this. In the invention, different types of drape adaptors may be respectively used for attaching a surgical instrument a robot arm and for attaching an endoscope adaptor to a robot arm.

In first and second embodiments described above, the case has been described in which the adaptor 7 (the drape adaptor) and the drape 12 are provided independently of each other. However, the invention is not limited thereto. In the invention, a drape adaptor and a drape may be integrally provided.

Also, in a second embodiment described above, the case has been described in which the rotation prevention member 762 is configured to be in contact with the shaft 65*d* (drive transmission shaft) to prevent the rotation of the shaft 65*d* (drive transmission shaft), so as to prevent the rotation of the endoscope holder 61. However, the invention is not limited to this. In the invention, a rotation prevention member may be configured to prevent rotation of a drive transmission shaft by a non-contact method with the drive transmission shaft so as to prevent rotation of an endoscope holder.

Also, in a second embodiment described above, the case has been described in which the rotation prevention member 762 is configured to prevent the rotation of the shaft 65*d* (drive transmission shaft) due to friction between the portions where the rotation prevention member 762 and the shaft 65*d* (drive transmission shaft) are in contact with each other, so as to prevent the rotation of the endoscope holder 61. However, the invention is not limited to this. In the invention, a rotation prevention member may be configured to prevent rotation of a drive transmission shaft by electromagnetic force or the like so as to prevent rotation of an endoscope holder.

Also, in a second embodiment described above, the case has been described in which the pair of second protruding portions 962*j* (protruding portion) abut on the inner surface 762*a* of the base portion 62, to restrict the rotation of the holding portion 962. However, the invention is not limited to this. In the invention, a holding portion may be fixed to an inner surface of a base portion.

Figure 25:
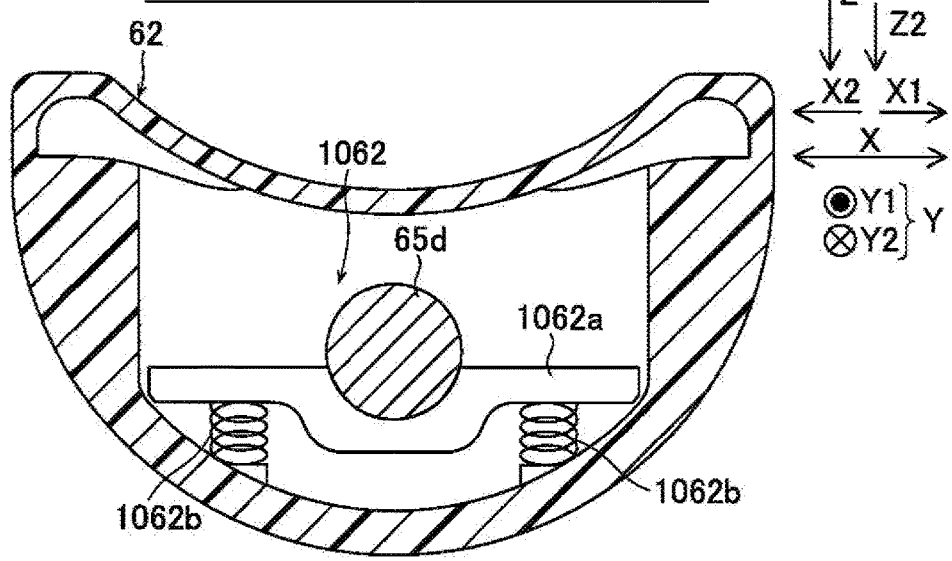
FIG. 25 is a diagram illustrating a cross sectional view of a rotation prevention member of an endoscope adaptor according to a first modification of a second embodiment.

Also, in a second embodiment described above, the case has been described in which the rotation prevention member 762 includes: the braking part 862 that is in contact with the outer circumference of the shaft 65*d* (drive transmission shaft) with surrounding the outer circumference of the shaft 65*d*; and the holding portion 962 that is provided inside of the base portion 62, holds the braking part 862, and abuts on the internal portion of the base portion 62. However, the invention is not limited to this. In the invention, like a first modification as illustrated in FIG. 25, a shaft 65*d* (drive transmission shaft) may be provided in a base portion 62. And a rotation prevention member 1062 may include a braking portion 1062*a* to be in contact with the shaft 65*d* (drive transmission shaft); and a pair of bias members 1062*b* which is provided inside of the base portion 62 and presses the braking portion 1062*a* against the shaft 65*d* (drive transmission shaft). As a result, the rotation of the shaft 65*d* can be prevented by simply pressing the braking portion 1062a against the shaft 65d using the bias members 1062b, so that the structure of the rotation prevention member 1062 can be simplified.

Figure 26:
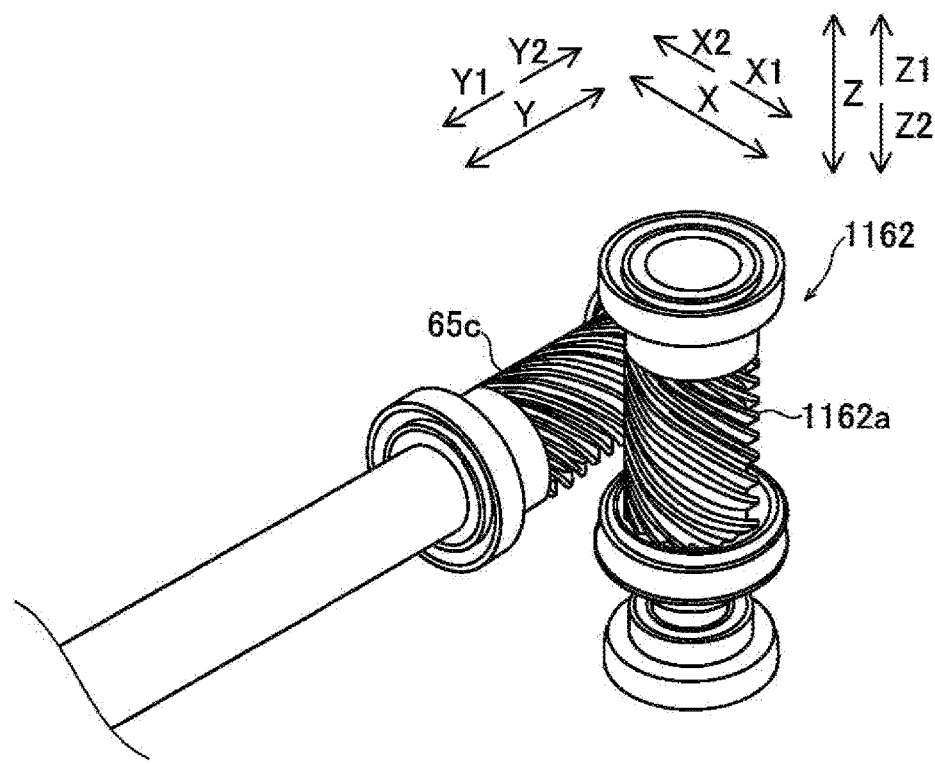
FIG. 26 is a diagram illustrating a perspective view of a rotation prevention member of an endoscope adaptor according to a second modification of a second embodiment.

Also, in a second embodiment described above, the case has been described in which the rotation prevention member 762 includes: the braking part 862 that is in contact with the outer circumference of the shaft 65d (drive transmission shaft) with surrounding the outer circumference of the shaft 65d; and the holding portion 962 that is provided inside of the base portion 62, holds the braking part 862, and abuts on the internal portion of the base portion 62. However, the invention is not limited to this. In the invention, like a second modification as illustrate in FIG. 26, a rotation prevention member 1162 may be composed of a cylindrical worm 65c extending in a Y direction and a cylindrical worm 1162a extending in a Z direction.

Also, in a second embodiment described above, the case has been described in which the rotation prevention member 762 prevents the rotation of the shaft 65d (drive transmission shaft). However, the invention is not limited to this. In the invention, a rotation prevention member may prevent rotation of an endoscope by directly contacting with the endoscope.

The invention claimed is:

1. An endoscope adaptor to be detachably connected to a robot arm of a robotic surgical system through a drape adaptor holding a drape, the endoscope adaptor comprising:
   an endoscope holder that holds an endoscope; and
   a base rotatably supporting the endoscope holder, the base being provided with: a driven member rotatably provided in the base and engaged directly or indirectly with a drive part of the robot arm to be rotated by the drive part of the robot arm via the drape adaptor; and
   a transmission mechanism that includes a drive transmission shaft to transmit rotation of the driven member to the endoscope holder, wherein
   the base further includes a cable holder that holds a cable connected to the endoscope.

2. The endoscope adaptor according to claim 1, wherein the cable holder includes an elastic member to hold the cable.

3. The endoscope adaptor according to claim 2, wherein the cable holder includes a holding member including an accommodation space in which the elastic member is held, wherein the holding member is configured to transition between a first state in which the holding member is engaged with the base while holding the elastic member in the accommodation space and a second state in which the holding member is disengaged from the base while holding the elastic member in the accommodation space.

4. The endoscope adaptor according to claim 3, wherein the holding member is attached to the base in such a manner that the holding member is rotatable with respect to the base about a rotation axis extending in a direction parallel with a longitudinal direction of the base, and
   the holding member includes an elastically deformable portion that is engaged with the base in the first state by being elastically deformed and is disengaged from the base in the second state by being elastically deformed.

5. The endoscope adaptor according to claim 3, wherein the holding member includes:
   a rotation shaft for rotating the holding member about a rotation axis extending in a direction parallel to a longitudinal direction of the base; and
   a support portion that is protruded from the base and rotatably supports the rotation shaft.

6. The endoscope adaptor according to claim 3, wherein the elastic member is detachably attached to the holding member.

7. The endoscope adaptor according to claim 1, wherein the cable holder includes an elastic member that includes a through hole that penetrates the elastic member, and the through hole comprises:
   a first hole portion in which a light cable connected to the endoscope is configured to be inserted; and
   a second hole portion in which a camera cable connected to the endoscope is configured to be inserted, wherein the second hole portion has a diameter smaller than that of the first hole portion.

8. The endoscope adaptor according to claim 1, wherein the endoscope holder includes an engagement portion configured to engage with an engagement portion of the endoscope.

9. The endoscope adaptor according to claim 1, wherein the endoscope holder includes an engagement portion configured to engage with an engagement portion of the endoscope, and
   the engagement portion of the endoscope holder comprises a notch which is recessed in the endoscope holder toward an insertion direction of the endoscope in which the endoscope is inserted to the endoscope holder and is configured to engage with an operation part which protrudes from an outer circumferential surface of the endoscope and serves as the engagement portion of the endoscope.

10. The endoscope adaptor according to claim 9, wherein the notch is configured to position the endoscope to a predetermined position in the insertion direction with the engagement portion of the endoscope holder and the engagement portion of the endoscope being engaged with each other.

11. The endoscope adaptor according to claim 1, wherein the endoscope holder includes a holder-side protrusion that protrudes in a first direction opposite to a second direction in which an endoscope-side protrusion of the endoscope protrudes and that is configured to engage with the endoscope-side protrusion of the endoscope, wherein the second direction is orthogonal to a rotation axis of the endoscope, and
   the holder-side protrusion is configured to generate a sound upon engaging with or disengaging from the endoscope-side protrusion.

12. The endoscope adaptor according to claim 11, wherein the holder-side protrusion is configured to elastically deform by abutting on the endoscope-side protrusion to thereby generate the sound when the holder-side protrusion moves over the endoscope-side protrusion and engages with or disengages from the endoscope-side protrusion.

13. The endoscope adaptor according to claim 1, wherein the cable holder is provided on a surface of the base that faces away from the endoscope in a direction of a rotation axis of the driven member.

14. The endoscope adaptor according to claim 1, wherein
a first gear is connected to the endoscope holder,
a second gear is connected to the driven member,
the transmission mechanism comprises:
   a third gear meshed with the first gear;
   a fourth gear meshed with the second gear; and the drive transmission shaft to which the third gear and the fourth gear are connected and which is configured to be rotated by the rotation of the driven member, and the base further includes a rotation prevention member configured to prevent rotation of the endoscope holder when the driven member is not driven by the drive part of the robot arm.

15. The endoscope adaptor according to claim 14, wherein
the rotation prevention member is configured to be in contact with the drive transmission shaft to prevent rotation of the drive transmission shaft so as to prevent the rotation of the endoscope holder.

16. The endoscope adaptor according to claim 15, wherein
the rotation prevention member is configured to prevent the rotation of the drive transmission shaft by friction between portions where the rotation prevention member and the drive transmission shaft are in contact with each other, so as to prevent the rotation of the endoscope holder.

17. The endoscope adaptor according to claim 16, wherein
the drive transmission shaft is provided inside of the base, and
the rotation prevention member includes:
a braking part that is in contact with an outer circumference of the drive transmission shaft as surrounding the outer circumference of the drive transmission shaft; and
a holding portion that is provided inside the base, holds the braking part, and abuts on an internal portion of the base.

18. The endoscope adaptor according to claim 17, wherein
the base includes an inner surface of the base that faces the drive transmission shaft,
the holding portion includes a pair of protruding portions that projects outward in radial directions of the drive transmission shaft, and
the pair of protruding portions of the holding portion are in contact with the inner surface of the base.

19. The endoscope adaptor according to claim 16, wherein
the drive transmission shaft is provided inside the base, and
the rotation prevention member includes:
a braking part that is provided at a position to be in contact with the drive transmission shaft; and
a bias member that is provided inside the base and is configured to press the braking part against the drive transmission shaft.

20. The endoscope adaptor according to claim 15, wherein
the rotation prevention member is configured to prevent the drive transmission shaft from rotating when a torque applied to the drive transmission shaft is smaller than a predetermined torque as the driven member is not rotationally driven by the drive part of the robot arm and allows the drive transmission shaft to rotate when the driven member is rotationally driven by the drive part of the robot arm and a torque equal or greater than the predetermined torque is applied to the drive transmission shaft.

* * * * *